United States Patent
Fischer

(10) Patent No.: US 9,949,160 B2
(45) Date of Patent: Apr. 17, 2018

(54) INTER-FREQUENCY BIAS COMPENSATION FOR TIME DIFFERENCE MEASUREMENTS IN POSITION DETERMINATIONS

(71) Applicant: QUALCOMM Incorporated, San Diego, CA (US)

(72) Inventor: Sven Fischer, Nuremberg (DE)

(73) Assignee: QUALCOMM Incorporated, San Diego, CA (US)

( * ) Notice: Subject to any disclaimer, the term of this patent is extended or adjusted under 35 U.S.C. 154(b) by 180 days.

(21) Appl. No.: 14/843,738

(22) Filed: Sep. 2, 2015

(65) Prior Publication Data

US 2016/0234709 A1 Aug. 11, 2016

Related U.S. Application Data

(60) Provisional application No. 62/113,052, filed on Feb. 6, 2015.

(51) Int. Cl.
*H04W 24/10* (2009.01)
*H04W 4/02* (2018.01)
(Continued)

(52) U.S. Cl.
CPC ............ *H04W 24/10* (2013.01); *H04W 4/02* (2013.01); *H04W 24/08* (2013.01); *H04W 4/025* (2013.01); *H04W 64/00* (2013.01)

(58) Field of Classification Search
None
See application file for complete search history.

(56) References Cited

U.S. PATENT DOCUMENTS

| 2002/0098839 A1* | 7/2002 | Ogino | G01S 5/02 |
| | | | 455/424 |
| 2005/0037786 A1* | 2/2005 | Edge | H04W 56/002 |
| | | | 455/502 |

(Continued)

FOREIGN PATENT DOCUMENTS

EP 2666327 A1 11/2013

OTHER PUBLICATIONS

Fischer, Sven, "Introduction to OTDOA on LTE Networks", Qualcomm Technologies, Inc., Aug. 7, 2014, pp. 1-18.*

(Continued)

*Primary Examiner* — Benjamin Lamont
(74) *Attorney, Agent, or Firm* — Thien T. Nguyen

(57) ABSTRACT

A method for use in determining a position of a mobile device in a wireless communication network includes acquiring, by the mobile device, a first positioning signal transmitted at a first frequency and a second positioning signal transmitted at a second frequency that is different than the first frequency. The mobile device performs a first measurement of a time difference of arrival between the first positioning signal and the second positioning signal. In certain implementations, in response to a determination to not apply an inter-frequency bias compensation to the first measurement for inter-frequency related delays corresponding to the first frequency, the second frequency, or both the first frequency and the second frequency, the mobile device sends the first measurement and a first measurement description to a server to determine the position of the mobile device. The first measurement description indicates that the first measurement has not been compensated for the inter-frequency related delays.

26 Claims, 10 Drawing Sheets

(51) Int. Cl.
*H04W 24/08* (2009.01)
*H04W 64/00* (2009.01)

(56) References Cited

U.S. PATENT DOCUMENTS

| | | | |
|---|---|---|---|
| 2012/0083221 A1 | 4/2012 | Ranta-Aho et al. | |
| 2012/0182874 A1* | 7/2012 | Siomina | H04W 56/004 370/241 |
| 2015/0195674 A1* | 7/2015 | Opshaug | H04W 4/02 455/456.6 |
| 2015/0257121 A1* | 9/2015 | Siomina | H04W 64/003 455/456.6 |
| 2016/0157053 A1* | 6/2016 | Zhang | H04W 64/00 455/456.1 |

OTHER PUBLICATIONS

3$^{rd}$ Generation Partnership Project; Technical Specification Group Radio Access Network; Evolved Universal Terrestrial Radio Access (E-UTRA); LTE Positioning Protocol (LPP) (Release 12), 3GPP TS 36.55 v12.3.0, Dec. 2014, pp. 1-126.*
Fischer S., "Observed Time Difference of Arrival (OTDOA) Positioning in 3GPP LTE", Qualcomm Technologies, inc., Jun. 6, 2014, pp. 1-62.
3GPP TS 36.355, "LTE; Evolved Universal Terrestrial Radio Access (E-UTRA); LTE Positioning Protocol (LPP) (3GPP TS 36.355 version 12.3.0 Release 12)", Technical Specification, European Telecommunications Standards Institute (EISI), 650, Route Des Lucioles; F-06921 Sophia-Antipolis ; France, val. 3GPP RAN 2, No. V12.3.0, Feb. 1, 2015 (Feb. 1, 2015), XP014248585, 128 Pages.
3GPP TS 36.355, "LTE; Evolved Universal Terrestrial Radio Access (E-UTRA); LTE Positioning Protocol (LPP) (3GPP TS 36.355 version 12.3.0 Release 12)", Technical Specification, European Telecommunications Standards Institute (ETSI), 650, Route Des Lucioles; F-06921 Sophia-Antipolis ; France, val. 3GPP RAN 2, No. V12.3.0, Feb. 1, 2015 (Feb. 1, 2015), XP014248585, 128 Pages.
International Search Report and Written Opinion—PCT/US2016/016184—ISA/EPO—dated May 3, 2016.

* cited by examiner

INTER-FREQUENCY BIAS COMPENSATION FOR TIME DIFFERENCE MEASUREMENTS IN POSITION DETERMINATIONS

CROSS-REFERENCE TO RELATED APPLICATION

The present application for patent claims the benefit of U.S. Provisional Application No. 62/113,052, entitled "INTER-FREQUENCY BIAS COMPENSATION FOR TIME DIFFERENCE MEASUREMENTS IN POSITION DETERMINATIONS," filed Feb. 6, 2015, assigned to the assignee hereof, and expressly incorporated herein by reference in its entirety.

FIELD OF DISCLOSURE

This disclosure relates generally to mobile communications and, in particular but not exclusively, relates to determining, at least in part, a position of wireless mobile devices.

BACKGROUND

The position of a mobile device (device), such as, for example, a cellular telephone, may be estimated based on information gathered from various systems. One such system may include the Global Positioning System (GPS), which is one example of a satellite positioning system (SPS). SPS systems such as GPS may include a number of space vehicles (SV) orbiting the earth. Another example of a system that may provide a basis for estimating the position of a mobile device is a cellular communication system including a number of base stations to support communications for a number of mobile devices.

A position estimate, which may also be referred to as a position "fix", for a mobile device may be obtained, for example, based at least in part on distances or ranges from the mobile device to one or more transmitters, and also based at least in part on the locations of the one or more transmitters. Such transmitters may comprise SVs in the case of an SPS and/or terrestrial base stations in the case of a cellular communication system, for example. Ranges to the transmitters may be based on one or more signals transmitted by the transmitters and received at the mobile device, and/or vice versa. The location of the transmitters may be ascertained, in at least some example implementations, based on the identities of the transmitters, which may be ascertained from one or more signals received from the transmitters.

In certain Code Division Multiple Access (CDMA) digital cellular networks, a position location capability may apply Advanced Forward Link Trilateration (AFLT) techniques. In certain example Wideband Code Division Multiple Access (WCDMA) and Long Term Evolution (LTE) networks a position location capability may apply Observed Time Difference Of Arrival (OTDOA) techniques.

LTE OTDOA positioning technology, by way of example, may use Positioning Reference Signals (PRS) to determine (e.g., measure, calculate, estimate, etc.) a Time Difference of Arrival (TOA) for the positioning signals received from neighboring cells to determine an OTDOA. In order to be able to measure the PRS signals from the serving cell and neighbor cells, a mobile device, may send an assistance data request to an OTDOA system server. Such a server may then send certain assistance data, e.g., possible indicating a suite of cells' information (e.g., Base Station Almanac (BSA) and timing information), to the mobile device. In this example, at least a portion of the information provided to the mobile device by way of such example assistance data may help the mobile device to identify which PRS(s) (cells, transceivers, etc.) to attempt to use for TOA measurements. Note, the terms mobile device, user equipment (UE), and mobile station (MS) are used interchangeably herein and unless otherwise specified are intended to cover any type of electronic device that may participate in the example techniques and/or systems provided herein.

In some instances, an OTDOA measurement may comprise a Reference Signal Time Difference (RSTD). An RSTD may, for example, indicate a relative timing difference between two cells (e.g., a reference cell and a neighbour cell), calculated as the smallest time difference between two subframe boundaries received from the two different cells. The PRS signals may be transmitted by their respective cells on the same carrier frequency (herein, referred to intra-frequency). In other instances, the PRS signals may be transmitted on different carrier frequencies (herein, referred to as inter-frequency). Thus, an RSTD measurement may be calculated for both "intra-frequency" PRS signals and "inter-frequency" PRS signals.

Such TOA-based measurements may be related to the geometric distance between an antenna of the mobile device and an antenna of the transmitting base station. In certain instances, however, frequency components of a positioning signal may encounter a time delay (herein, referred to as group delay), e.g., while being processed by circuitry in a device, such as an amplifier, while propagating through a medium such as air, etc. When performing intra-frequency measurements, a group delay of each signal transmitted on the same frequency may be the same and thus, may be easily discounted. However, when performing inter-frequency measurements, accurate positioning may be difficult to achieve without compensating in some manner for the different delays encountered by the differing frequencies of the positioning signals.

Some systems may attempt to provide inter-frequency compensation by including a static look-up table in the mobile device which may include various inter-frequency bias compensation values for the carrier frequencies that a particular mobile device supports. However, the group delays encountered by certain frequencies may vary over time, for example, due in-part to changing environmental factors, such as temperature. Thus, an inaccurate bias compensation may be applied at times, which may reduce the accuracy of such inter-frequency measurements, and possibly the accuracy of a corresponding position fix for the mobile device.

SUMMARY

The following presents a simplified summary relating to one or more aspects and/or embodiments disclosed herein. As such, the following summary should not be considered an extensive overview relating to all contemplated aspects and/or embodiments, nor should the following summary be regarded to identify key or critical elements relating to all contemplated aspects and/or embodiments or to delineate the scope associated with any particular aspect and/or embodiment. Accordingly, the following summary has the sole purpose to present certain concepts relating to one or more aspects and/or embodiments relating to the mechanisms disclosed herein in a simplified form to precede the detailed description presented below.

Aspects of the present disclosure include a method, an apparatus, a mobile device, a server, and a non-transitory computer-readable medium for assisting or otherwise determining the position of the mobile device based on inter-frequency positioning signal TOA measurements.

For example, according to one aspect, a method for use in determining a position of a mobile device in a wireless communication network includes acquiring, by the mobile device, a first positioning signal transmitted at a first frequency and a second positioning signal transmitted at a second frequency that is different than the first frequency. The mobile device performs a first measurement of a time difference of arrival between the first positioning signal and the second positioning signal. In response to a determination to not apply an inter-frequency bias compensation to the first measurement for inter-frequency related delays corresponding to the first frequency, the second frequency, or both the first frequency and the second frequency, the mobile device sends the first measurement and a first measurement description to a server to determine the position of the mobile device. The first measurement description indicates that the first measurement has not been compensated for the inter-frequency related delays.

According to another aspect, a method for use in a server having a computing platform, includes obtaining a first measurement of a time difference of arrival between a first positioning signal and a second positioning signal as determined by a mobile device; the first positioning signal having been transmitted at a first frequency and the second positioning signal having been transmitted at a second frequency that is different than the first frequency. The method also includes obtaining a measurement description from the mobile device. Then, in response to a determination that the measurement description indicates that the first measurement has not been compensated, by the mobile device, for inter-frequency related delays corresponding to the first frequency, the second frequency, or both the first frequency and the second frequency, the computing platform determines an inter-frequency bias compensation for the inter-frequency related delays corresponding to the first measurement, applies the inter-frequency bias compensation to the first measurement to generate a compensated measurement, and determines, at least in part, a position of the mobile device based, at least in part, on the compensated measurement.

According to yet another aspect, a mobile device for assisting in the determination of a position of the mobile device in a wireless communication network includes memory adapted to store program code and a processing unit coupled to the memory to access and execute instructions included in the program code. The instructions are configured to acquire a first positioning signal transmitted at a first frequency and a second positioning signal transmitted at a second frequency that is different than the first frequency and perform a first measurement of a time difference of arrival between the first positioning signal and the second positioning signal. The instructions are further configured to, in response to a determination, at the mobile device, to not apply an inter-frequency bias compensation to the first measurement for inter-frequency related delays corresponding to the first frequency, the second frequency, or both the first frequency and the second frequency, send the first measurement and a first measurement description to a server to determine the position of the mobile device. The first measurement description indicates that the first measurement has not been compensated, at the mobile device, for the inter-frequency related delays.

In another aspect, a server for assisting in the determination of a position of a mobile device in a wireless communication network includes memory adapted to store program code and a processing unit coupled to the memory to access and execute instructions included in the program code. The instructions are configured to direct the location server to obtain a measurement description and a first measurement of a time difference of arrival between a first positioning signal and a second positioning signal as determined by the mobile device, the first positioning signal having been transmitted at a first frequency and the second positioning signal having been transmitted at a second frequency that is different than the first frequency. The instructions are further configured to direct the location server to, in response to a determination that the measurement description indicates that the first measurement has not been compensated, by the mobile device, for inter-frequency related delays corresponding to the first frequency, the second frequency, or both the first frequency and the second frequency: (i) determine an inter-frequency bias compensation for the inter-frequency related delays corresponding to the first measurement; (ii) apply the inter-frequency bias compensation to the first measurement to generate a compensated measurement; and (iii) determine, at least in part, the position of the mobile device based, at least in part, on the compensated measurement.

In yet another aspect, a mobile device for assisting in the determination of a position of the mobile device in a wireless communication network, includes means for acquiring a first positioning signal transmitted at a first frequency and a second positioning signal transmitted at a second frequency that is different than the first frequency; means for performing a first measurement of a time difference of arrival between the first positioning signal and the second positioning signal; and means for sending the first measurement and a first measurement description to a server to determine the position of the mobile device in response to a determination, at the mobile device, to not apply an inter-frequency bias compensation to the first measurement for inter-frequency related delays corresponding to the first frequency, the second frequency, or both the first frequency and the second frequency. The first measurement description indicates that the first measurement has not been compensated, at the mobile device, for the inter-frequency related delays.

In another aspect, a server for assisting in the determination of a position of a mobile device in a wireless communication network includes means for obtaining a first measurement of a time difference of arrival between a first positioning signal and a second positioning signal as determined by the mobile device, the first positioning signal having been transmitted at a first frequency and the second positioning signal having been transmitted at a second frequency that is different than the first frequency; means for obtaining a measurement description from the mobile device; means for determining an inter-frequency bias compensation for inter-frequency related delays corresponding to the first frequency, the second frequency, or both the first frequency and the second frequency in response to a determination that the measurement description indicates that the first measurement has not been compensated, by the mobile device, for the inter-frequency related delays; means for applying the inter-frequency bias compensation to the first measurement to generate a compensated measurement in response to the determination that the measurement description indicates that the first measurement has not been compensated; and means for determining, at least in part, the position of the mobile device based, at least in part, on the compensated measurement in response to the determination that the measurement description indicates that the first measurement has not been compensated.

Another aspect includes a non-transitory computer-readable medium that includes program code stored thereon for use in determining a position of a mobile device in a wireless communication network. The program code includes instructions to acquire a first positioning signal transmitted at a first frequency and a second positioning signal transmitted at a second frequency that is different than the first frequency and to perform a first measurement of a time difference of arrival between the first positioning signal and the second positioning signal. The program code further includes instructions to, in response to a determination, at the mobile device, to not apply an inter-frequency bias compensation to the first measurement for inter-frequency related delays corresponding to the first frequency, the second frequency, or both the first frequency and the second frequency, send the first measurement and a first measurement description to a server to determine the position of the mobile device, wherein the first measurement description indicates that the first measurement has not been compensated, at the mobile device, for the inter-frequency related delays.

In yet another aspect, a non-transitory computer-readable medium includes program code stored thereon for use in determining a position of a mobile device in a wireless communication network. The program code includes instructions to obtain, at a server, a first measurement of a time difference of arrival between a first positioning signal and a second positioning signal as determined by the mobile device, the first positioning signal having been transmitted at a first frequency and the second positioning signal having been transmitted at a second frequency that is different than the first frequency. The program code further includes instructions to obtain, at the server, a measurement description from the mobile device, and, in response to a determination that the measurement description indicates that the first measurement has not been compensated, by the mobile device, for inter-frequency related delays corresponding to the first frequency, the second frequency, or both the first frequency and the second frequency to (i) determine an inter-frequency bias compensation for the inter-frequency related delays corresponding to the first measurement; (ii) apply the inter-frequency bias compensation to the first measurement to generate a compensated measurement; and (iii) determine, at least in part, the position of the mobile device based, at least in part, on the compensated measurement.

In still another aspect, a method may be provided for use in a mobile device, which comprises, at the mobile device: acquiring a first positioning signal transmitted at a first frequency and a second positioning signal transmitted at a second frequency that is different than the first frequency; performing a measurement of a time difference of arrival between the first positioning signal and the second positioning signal; and sending the measurement and a measurement description to a location server, wherein the measurement description indicates that the measurement has not been compensated, at the mobile device, for inter-frequency related delays corresponding to the first frequency, the second frequency, or both the first frequency and the second frequency.

In yet another aspect, a method may be provided for use in a mobile device, which comprises, at the mobile device: acquiring a first positioning signal transmitted at a first frequency and a second positioning signal transmitted at a second frequency that is different than the first frequency; performing a measurement of a time difference of arrival between the first positioning signal and the second positioning signal; and applying an inter-frequency bias compensation to the measurement to generate a compensated measurement, the inter-frequency bias compensation to reduce inter-frequency related delays corresponding to the first frequency, the second frequency, or both the first frequency and the second frequency; and sending the compensated measurement and a measurement description to a location server, wherein the measurement description indicates that the compensated measurement has been compensated, at the mobile device, for the inter-frequency related delays.

In certain further aspects, an apparatus for use in a mobile device may be provided which comprises: means for acquiring a first positioning signal transmitted at a first frequency and a second positioning signal transmitted at a second frequency that is different than the first frequency; means for performing a measurement of a time difference of arrival between the first positioning signal and the second positioning signal; and means for sending the measurement and a measurement description to a location server, wherein the measurement description indicates that the measurement has not been compensated, at the mobile device, for inter-frequency related delays corresponding to the first frequency, the second frequency, or both the first frequency and the second frequency.

In certain further aspects, an apparatus for use in a mobile device may be provided which comprises: means for acquiring a first positioning signal transmitted at a first frequency and a second positioning signal transmitted at a second frequency that is different than the first frequency; means for performing a measurement of a time difference of arrival between the first positioning signal and the second positioning signal; means for applying an inter-frequency bias compensation to the measurement to generate a compensated measurement, the inter-frequency bias compensation to reduce inter-frequency related delays corresponding to the first frequency, the second frequency, or both the first frequency and the second frequency; and means for sending the compensated measurement and a measurement description to a location server, wherein the measurement description indicates that the compensated measurement has been compensated, at the mobile device, for the inter-frequency related delays.

In certain other aspects, a mobile device may be provided which comprises memory adapted to store program code, and a processing unit coupled to the memory to access and execute instructions included in the program code to direct the mobile device to: acquire a first positioning signal transmitted at a first frequency and a second positioning signal transmitted at a second frequency that is different than the first frequency; perform a measurement of a time difference of arrival between the first positioning signal and the second positioning signal; and send the measurement and a measurement description to a location server, wherein the measurement description indicates that the measurement has not been compensated, at the mobile device, for inter-frequency related delays corresponding to the first frequency, the second frequency, or both the first frequency and the second frequency.

In certain other aspects, a mobile device may be provided which comprises memory adapted to store program code, and a processing unit coupled to the memory to access and execute instructions included in the program code to direct the mobile device to: acquire a first positioning signal transmitted at a first frequency and a second positioning signal transmitted at a second frequency that is different than the first frequency; perform a measurement of a time difference of arrival between the first positioning signal and the second positioning signal; apply an inter-frequency bias compensation to the measurement to generate a compensated measurement, the inter-frequency bias compensation to reduce inter-frequency related delays corresponding to the first frequency, the second frequency, or both the first frequency and the second frequency; and send the compensated measurement and a measurement description to a location server, wherein the measurement description indicates that the compensated measurement has been compensated, at the mobile device, for the inter-frequency related delays.

In still other aspects, a non-transitory computer-readable medium may be provided which includes program code stored thereon for use in determining a position of a mobile device in a wireless communication network, the program code comprising instructions to: acquire a first positioning signal transmitted at a first frequency and a second positioning signal transmitted at a second frequency that is different than the first frequency; perform a measurement of a time difference of arrival between the first positioning signal and the second positioning signal; and send the measurement and a measurement description to a location server, wherein the measurement description indicates that the measurement has not been compensated, at the mobile device, for inter-frequency related delays corresponding to the first frequency, the second frequency, or both the first frequency and the second frequency.

In some other aspects, a non-transitory computer-readable medium may be provided which includes program code stored thereon for use in determining a position of a mobile device in a wireless communication network, the program code comprising instructions to: acquire a first positioning signal transmitted at a first frequency and a second positioning signal transmitted at a second frequency that is different than the first frequency; perform a measurement of a time difference of arrival between the first positioning signal and the second positioning signal; apply an inter-frequency bias compensation to the measurement to generate a compensated measurement, the inter-frequency bias compensation to reduce inter-frequency related delays corresponding to the first frequency, the second frequency, or both the first frequency and the second frequency; and send the compensated measurement and a measurement description to a location server, wherein the measurement description indicates that the compensated measurement has been compensated, at the mobile device, for the inter-frequency related delays.

Other objects and advantages associated with the aspects and embodiments disclosed herein will be apparent to those skilled in the art based on the accompanying drawings and detailed description.

BRIEF DESCRIPTION OF THE DRAWINGS

The accompanying drawings are presented to aid in the description of various example embodiments and are provided solely for illustration of the embodiments and not limitation thereof.

DETAILED DESCRIPTION

Figure 1:
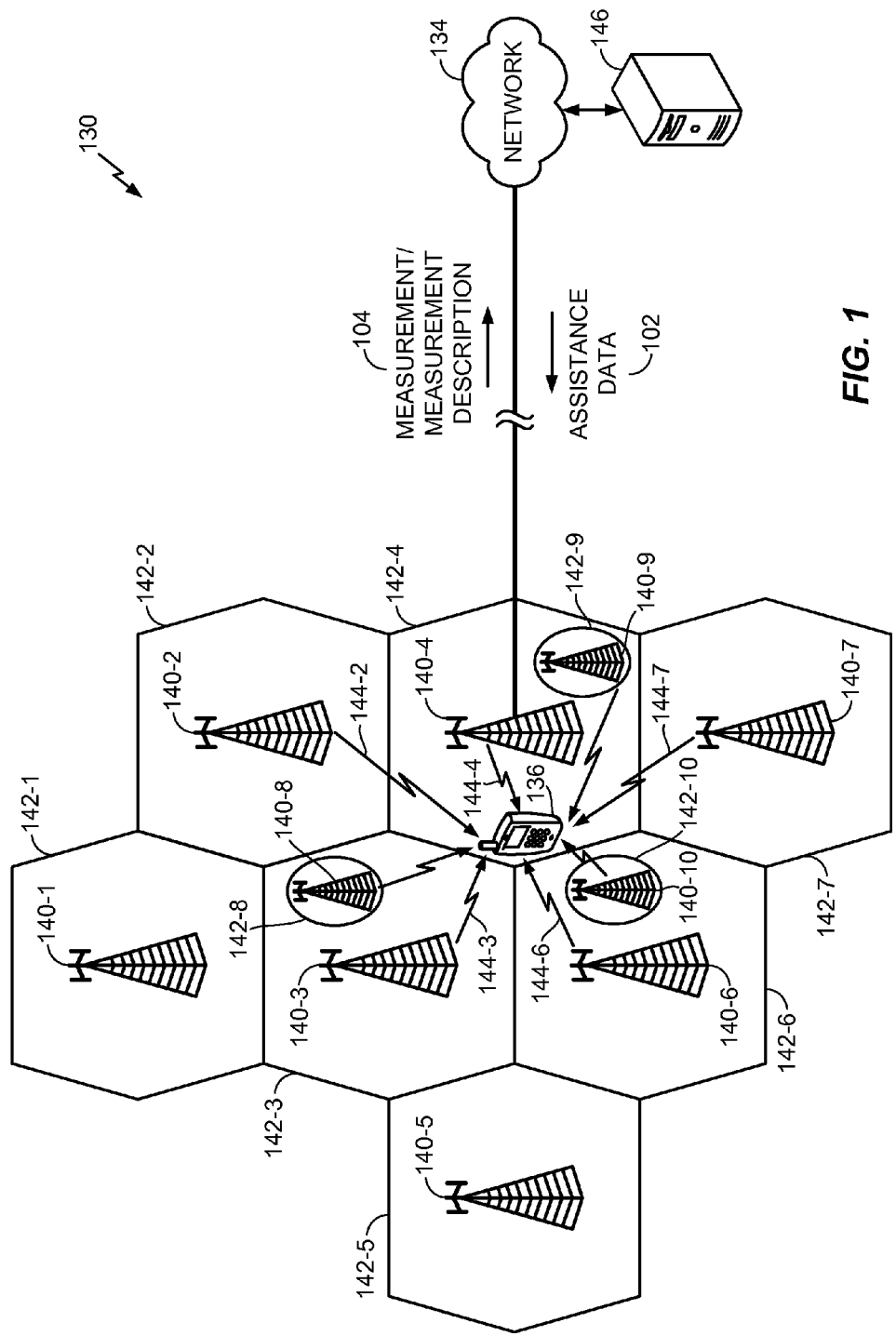
FIG. 1 is a functional block diagram of an example wireless communication network, in accordance with an example implementation.

Various aspects are disclosed in the following description and related drawings directed to some example embodiments. Alternate embodiments may be devised without departing from the scope of this description. Additionally, well-known elements may not be described in detail or will be omitted so as not to obscure the relevant details of example techniques presented herein.

The word "exemplary" is used herein to mean "serving as an example, instance, or illustration." Any embodiment described herein as "exemplary" is not necessarily to be construed as preferred or advantageous over other embodiments. Further, the interchangeable terms "embodiment" and "implementation" do not require that all embodiments/implementations include the discussed feature, advantage, mode of operation, etc.

The terminology used herein is for the purpose of describing particular embodiments only and is not intended to be limiting of embodiments. As used herein, the singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequence of actions described herein can be considered to be embodied entirely within any form of computer-readable storage medium having stored therein a corresponding set of computer instructions that upon execution would cause an associated processor to perform the functionality described herein. Thus, the various aspects presented herein may be embodied in a number of different forms, all of which have been contemplated to be within the scope of the claimed subject matter.

Although much of the description herein is drawn to examples in which a wireless communication system comprises a cellular communication system, it should be understood that the techniques provided herein may be applied in various manners within one or more other wireless communication systems. Thus, for example, techniques provided herein may be applied to or otherwise adapted to wireless networks having devices (e.g., access point devices, dedicated beacon transmitters, etc.) that transmit certain applicable types of position signals from known or discoverable locations. The terms "network" and "system" may be used interchangeably herein, as well, to represent the same aspect, for example, as in a wireless communication system and a wireless communication network.

FIG. 1 illustrates an example wireless communication network 130 according to one or more example embodiments. As shown, wireless communication network 130 includes a network of cells (e.g., cells 142-1 through 142-10), a network 134, a server 146 (e.g., representing all or part of one or more computing platforms), and one or more mobile devices 136. The cells (e.g., cells 142-1 through 142-10) may, for example, be configured to enable mobile device 136 to access services and devices associated with wireless communication network 130, possibly one or more external networks, such as the Public Switched Telephone Network (PSTN), the Internet, an intranet, etc., certain computing platform(s) or other like devices, or some combination thereof, which for the sake of this illustration may be represented, in whole or in part, by the cloud image of network 134.

Each cell (e.g., cells 142-1 through 142-10) may include at least one base station (e.g., base stations 140-1 through 140-10) or other like transceiver-configured access device. The base stations (e.g., base stations 140-1 through 140-10) may be geographically distributed across a wide geographic area served by wireless communication network 130. The base stations (e.g., base stations 140-1 through 140-10) may provide wireless coverage for one or more respective portions of that geographic area, referred to as cells (e.g., cells 142-1 through 142-10). Because of this, the mobile device 136 may move within or between cells (e.g., cells 142-1 through 142-10) and may communicate with one or more base stations (e.g., base stations 140-1 through 140-10) at a given position.

Different cells (e.g., cells 142-1 through 142-10) may have different nominal sizes/shapes, e.g., depending on the maximum transmit power utilized by the base stations (e.g., 140-1 through 140-10) serving those cells. For example, base station 140-1 may have a relatively large maximum transmit power and correspondingly serves mobile devices 136 within a relatively large cell 142-1, while base station 140-8 may have a relatively small maximum transmit power and correspondingly serves mobile devices 136 within a relatively small cell 142-8. In general, different base stations that have different pre-defined maximum transmit powers (and thereby serve cells of different nominal sizes) belong to different base station classes (e.g., a macro base station class, a micro base station class, a pico base station class, femto base station class, etc.).

Different base stations may operate on different carrier frequencies. For example, the base stations serving relatively large cells may operate on a certain carrier frequency F1 (for example, at 2 GHz), and base stations serving relatively small cells may operate on a carrier Frequency F2 (for example, at 3.5 GHz), different from carrier frequency F1. Such deployments with large cells (e.g., macro cells) and small cells (e.g., micro-, pico-,etc. cells) are often referred to as Heterogeneous Networks (HetNet). Using different carrier frequencies for the macro cell layer and small cell layer often simplifies network planning and reduces inter-cell interference. For example, it may avoid having a small cell layer interfere with a macro cell layer.

As shown in FIG. 1, mobile device 136, at its current illustrated position, may be served by base station 140-4 in the sense that the mobile device 136 may currently be configured to exchange data with the base station 140-4 (e.g., to place calls, access various services/networks, etc). Thus, base station 140-4 may transmit data to mobile device 136 on a particular frequency (referred to as the serving cell frequency) and over a particular bandwidth (known as the serving cell bandwidth). Thus, in this example, from the perspective of mobile device 136, base station 140-4 may be referred to as the serving base station and cell 142-4 is the serving cell. Other cells that may be geographically adjacent to or partially coincident with the serving cell 142-4 may be referred to as neighboring cells. In this example, all cells shown in FIG. 1 may be neighboring cells of cell 142-4, possibly with the exception of cells 142-1 and 142-5.

Each of the cells (e.g., cells 142-1 through 142-10) (via a respective base station) may periodically transmit a positioning signal (e.g., positioning signals 144-2, 144-3, 144-4, 144-6, and 144-7). A positioning signal may, for example, comprise a predetermined signal that may be known to both a cell transmitting that signal and, possibly with the aid of assistance data provided by the server 146, by mobile device 136 receiving the signal. Exemplary positioning signals 144-2, 144-3, 144-4, 144-6, and 144-7 may be transmitted on the same or different frequencies as one another. For example, positioning signal 144-2 may be transmitted by cell 142-2 on the same carrier frequency as positioning signal 144-3 that is transmitted by cell 142-3, while positioning signal 144-4 may be transmitted on a carrier frequency that is different from the carrier frequency used to transmit 144-6. A TOA measurement on positioning signals of the same frequency is referred to herein as an intra-frequency TOA measurement, while a TOA measurement on positioning signals of differing frequencies is referred to herein as an inter-frequency TOA measurement.

In some implementations a "carrier" may be defined in accordance with 3GPP TS 36.104 as "The modulated waveform conveying the E-UTRA or UTRA physical channels". The carrier frequency may be the center frequency of the transmitted positioning signal. In each operating band, there are multiple carrier frequencies possible (dependent on the particular standard, and region of the world), and the modulated positioning signal has a certain bandwidth. In operation, the mobile device tunes its radio to the desired carrier frequency, and demodulates the positioning signal. The carrier frequencies are usually arranged such that bands do not overlap. E.g., if carrier frequency f1 uses a single-sided bandwidth of B1, then the spectrum required to transmit this signal is +/−B1, centered at f1. A separate carrier frequency f2 must then be outside of the spectrum covered by f1+/−B1, otherwise the two transmitted signals at f1 and f2 would overlap and interfere with each other. The carrier frequencies that are allowed are defined in the particular standard. The standard makes sure that the allowed carrier frequencies "make sense" (e.g., do not result in overlapping spectra, or any other restrictions).

The positioning signals (e.g., positioning signals 144-2, 144-3, 144-4, 144-6, and 144-7) transmitted by the cells in this exemplary manner may be acquired by mobile device 136 and used to determine positioning signal measurements, which may be used, at least in part, to determine a position of mobile device 136. For example, certain positioning signal measurements may be used, e.g., applied in a known multilateration technique or the like to determine a relative or other like coordinate based position location (e.g., a geographic position, etc.) of mobile device 136.

In one embodiment, mobile device 136 may communicate with server 146 (e.g., possibly a location server) on network 134 for accomplishing, at least in part, such a purpose. Communication between mobile device 136 and server 146 may include, for example, one or more transactions between mobile device 136 and server 146. A transaction may pertain to a particular operation, such as the exchange of capabilities, the transfer of measurement(s) 104 (e.g., reference signal time difference (RSTD)) to server 146, the transfer of assistance data (AD) 102 from server 146 to mobile device 136 possibly for assisting mobile device 136 to perform certain positioning signal measurement(s), or the transfer of an optional measurement description 104 related those measurements (e.g., all or part of a determined position of mobile device 136), just to name a few examples.

Assistance data 102 may, for example, be generated or other obtained/stored by server 146 and transferred to the mobile device 136. Mobile device 136 may, in certain example implementations, attempt to determine one or more OTDOA measurements for one or more pairs of positioning signals (e.g., positioning signals 144-2, 144-3, 144-4, 144-6, and 144-7) from different cells (e.g., cells 142-1 through 142-10).

Figure 2:
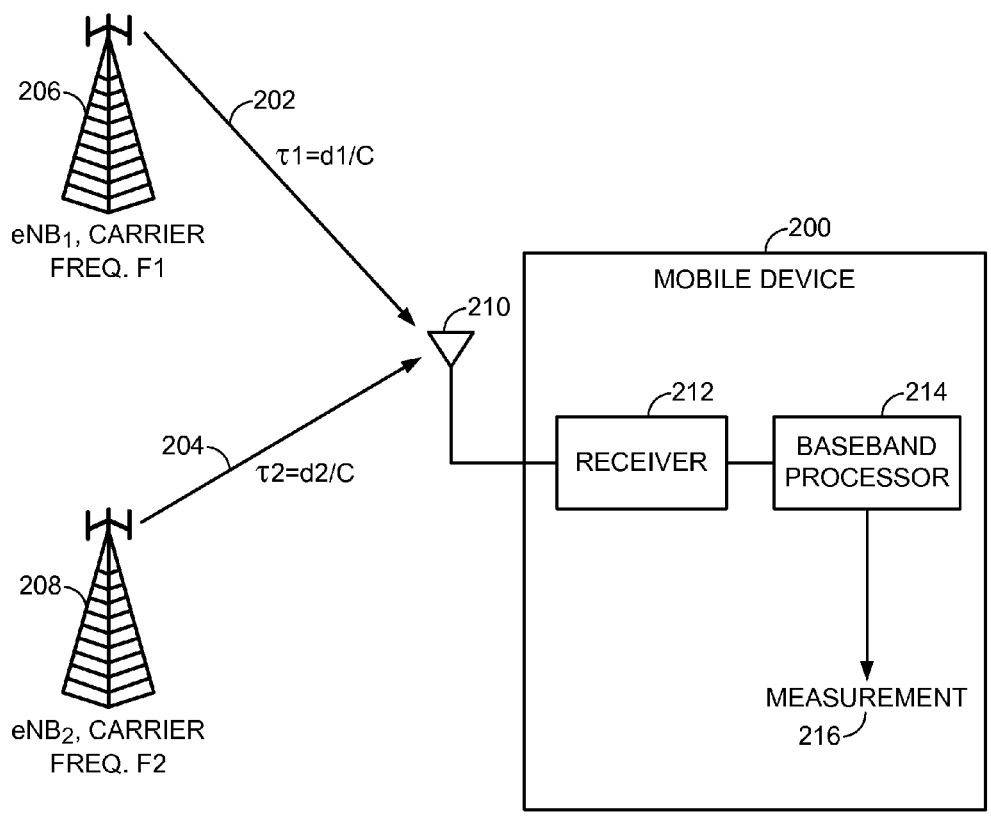
FIG. 2 is a functional block diagram of an example mobile device performing a measurement of a time difference of arrival of inter-frequency positioning signals, in accordance with an example implementation.

FIG. 2 is a functional block diagram of an exemplary mobile device 200 configured to perform an inter-frequency timing measurement of positioning signals 202 and 204 that are transmitted by respective base stations 206 and 208. Mobile device 200 represents a subset of features that may be provided in an example implementation of mobile device, such as, e.g., mobile device 136 of FIG. 1, while base stations 206 and 208 are illustrated examples representative of any of the base stations and/or other like transceiver devices that may be included in wireless communication network 130. More specifically, for this description, illustrated example of mobile device 200 includes an RF front end (e.g., represented by a receiver 212) and a baseband processor 214. As shown in FIG. 2, base station 206 may be configured to transmit positioning signal 202 on carrier frequency F1, while base station 208 may be configured to transmit positioning signal 204 on carrier frequency F2, which is a separate and distinct frequency from frequency F1. The measured TOA ($\tau$) of each positioning signal will be indicative of the respective time that it took for the respective positioning signal to propagate the distance between the antenna of the transmitting base station and the antenna of the receiving mobile device. By way of example, a TOA $\tau 1$ for positioning signal 202 may be expressed as $\tau 1 = d1/C$, where d1 is the distance between base station 206 and antenna 210, and where C is the speed of light (in a vacuum).

Similarly, a TOA $\tau 2$ for positioning signal 204 may be expressed as $\tau 2 = d2/C$, where d2 is the distance between base station 208 and antenna 210.

As mentioned above, when calculating a reference signal time difference (RSTD) for intra-frequency positioning signals, a group delay encountered by the positioning signals may be the same, and thus the mobile device 200 may subtract the measured TOAs, such that the RSTD measurement for positioning signals 202 and 204 is expressed as $RSTD_{2,1} = (d2-d1)/C$. However, when calculating an RSTD for inter-frequency positioning signals, it may be useful to account for TOA measurement effects due to the signals possibly experiencing different group delays. Thus, for inter-frequency, an example RSTD measurement for positioning signals 202 and 204 may be expressed as $RSTD_{2,1} = (d2-d1)/C + \Delta(F_1, F_2)$, where $\Delta(F_1, F_2)$ represents the inter-frequency bias caused by a group delay encountered by positioning signal 202 that may be different from that encountered by positioning signal 204. A measured RSTD for inter-frequency measurements (e.g., measurement 216) may, for example, be compensated in an attempt to more accurately correspond to the propagation distance difference. That is, different receiver chains (for different carrier frequencies) usually have different group delays, which may impact the RSTD measurement performance. Because of this, the desired (possibly minimum) performance requirements for inter-frequency RSTD measurements in some systems may be relaxed compared to intra-frequency measurements (e.g., +/−9 Ts for inter-frequency, compared to +/−5 Ts for intra-frequency RSTD measurements [3GPP TS 36.133], where Ts is the basic time unit in LTE and is equal to 1/(15000×2048) seconds, which is a little more than 32 ns (corresponding to about 9.8 meters). Therefore, inter-frequency RSTD measurement errors in some systems may be about twice as big as intra-frequency RSTD measurement errors.

Some systems may attempt to provide inter-frequency compensation by including a static look-up table in the mobile device (e.g., in memory) that includes various inter-frequency bias compensations for the carrier frequencies that the particular mobile device may support. In practice, this means that a mobile device may need to maintain a calibration table for different carrier frequency pairs to compensate for the RSTD measurements for the different group delays. With mobile devices supporting multiple frequency bands, such tables may become quite large, since the group delays may be different for each supported carrier frequency. In addition, such static calibration tables may be less than ideal, since group delays may vary with e.g., temperature, bandwidth and various implementation restrictions (e.g., variation of characteristics in high volume filter parts). Therefore, OTDOA positioning with inter-frequency RSTD measurements in some systems may be less accurate compared to the case when only intra-frequency RSTD measurements are used. However, in practical deployments, RSTD measurements are usually needed from base stations which operate on different carrier frequencies, as described above in relation to FIG. 1.

Accordingly, in accordance with certain aspects of the present disclosure some exemplary techniques are provided that may be used to support position determinations of a mobile device or for other purposes, and which make use of inter-frequency OTDOA measurements, and, for example, wherein an inter-frequency bias compensation may be (dynamically) calculated in response to an initial (likely uncompensated) determined OTDOA measurement. In one instance, for example, a server (e.g., a location server or the like) may be configured to solve for a frequency bias compensation in response to an initial determined OTDOA measurement (instead of trying to perform frequency bias compensation at the mobile device). That is, a mobile device inter-frequency group delay bias may be a common bias (common to the inter-frequency RSTD measurement performed on the same carrier frequency pair). This unknown bias can be added as an additional unknown to a cost function. The minimization of such a cost function (e.g., via a Taylor series estimation) may provide the estimated position of the mobile device as well as the mobile device frequency bias (with which the RSTD measurements would be corrected/compensated). With this approach, the inter-frequency OTDOA performance may be the same as, or approach that of, intra-frequency RSTD.

In one aspect, a mobile device (e.g., mobile device 136) may signal to the server 146 (e.g., a location server or the like), by way of a measurement description 104, as to whether or not the server is expected to solve for inter-frequency bias compensation, whether or not the mobile device may have already applied some form inter-frequency bias compensation to a one or more corresponding determined measurements, or both. For example, a measurement description may comprise a flag (e.g., one or more bits) in an LTE Positioning Protocol (LPP) message, such as the LPP Provide Location Information message that indicates to a server that a provided inter-frequency RSTD measurement (e.g., OTDOA measurement) has or has not been compensated for any group delay bias that may have occurred, e.g., due to a difference between frequencies of the positioning signals used in the determined OTDOA measurement.

In another aspect, certain similar (dynamic) inter-frequency bias determination capabilities as may be provided at a server (in whole or part) may instead or further also be implemented (in whole or part) at a mobile device for mobile device-based OTDOA. Indeed, in certain implementations, all or part of a position calculation may be performed by such a mobile device.

In some embodiments, inter-frequency bias may be treated as an additional unknown variable in the position calculation function. For example, as mentioned above, the Time-of-Arrival (TOA) values measured by the mobile device are related to the geometric distance between the mobile device and the base station. An N number of TOA values measured at the mobile device can be written as:

$$\hat{\tau}_1 = T_1 + \frac{d_1}{c} + \Delta_{f1} + \varepsilon_1 \quad \text{(EQ 1a)}$$

$$\hat{\tau}_2 = T_2 + \frac{d_2}{c} + \Delta_{f1} + \varepsilon_2 \quad \text{(EQ 1b)}$$

$$\vdots$$

$$\hat{\tau}_i = T_i + \frac{d_i}{c} + \Delta_{f1} + \varepsilon_i \quad \text{(EQ 1c)}$$

$$\hat{\tau}_{i+1} = T_{i+1} + \frac{d_{i+1}}{c} + \Delta_{f2} + \varepsilon_{i+1} \quad \text{(EQ 1d)}$$

$$\vdots$$

$$\hat{\tau}_N = T_N + \frac{d_N}{c} + \Delta_{f2} + \varepsilon_N \quad \text{(EQ 1e)}$$

where $\hat{\tau}_i$ is the TOA measured at the mobile for base station i;
$T_i$ is the transmit time at which the base station i transmits a downlink subframe;
$d_i$ is the distance between the antenna of the mobile device and antenna of the base station i;
c is the speed of the radio waves (speed of light);
$\Delta_{fi}$ is the group delay of the front-end for signals on carrier frequency $f_i$;
$\varepsilon_i$ is the measurement error due to noise, interference, etc.

In the above equations (1), it is assumed that the TOA measurements 1 to i are performed on one or more base station transmitted positioning signals on carrier frequency $f_1$; and the TOA measurements (i+1) to N are performed on one or more base station transmitted positioning signals on carrier frequency $f_2$.

In OTDOA location, the TOA's measured from neighbor base stations may be subtracted from the TOA measured from a reference base station. These TOA differences may be defined as OTDOA, or Reference Signal Time Difference (RSTD), since the TOA's are measured from reference signals, such as positioning reference signals, for example.

Defining the TOA measurement from the reference base station as $\hat{\tau}_1$, the OTDOA's may then be given by:

$$OTDOA_{2,1} = \hat{\tau}_2 - \hat{\tau}_1 = (T_2 - T_1) + \frac{d_2 - d_1}{c} + (\varepsilon_2 - \varepsilon_1) \quad \text{(EQ 2a)}$$

$$\vdots$$

$$OTDOA_{i,1} = \hat{\tau}_i - \hat{\tau}_1 = (T_i - T_1) + \frac{d_i - d_1}{c} + (\varepsilon_i - \varepsilon_1) \quad \text{(EQ 2b)}$$

$$OTDOA_{i+1,1} = \quad \text{(EQ 2c)}$$
$$\hat{\tau}_{i+1} - \hat{\tau}_1 = (T_{i+1} - T_1) + \frac{d_{i+1} - d_1}{c} + (\Delta_{f2} - \Delta_{f1}) + (\varepsilon_{i+1} - \varepsilon_1)$$

$$\vdots$$

$$OTDOA_{N,1} = \quad \text{(EQ 2d)}$$
$$\hat{\tau}_N - \hat{\tau}_1 = (T_N - T_1) + \frac{d_N - d_1}{c} + (\Delta_{f2} - \Delta_{f1}) + (\varepsilon_N - \varepsilon_1)$$

The equations (2) include the inter-frequency bias ($\Delta_{f2} - \Delta_{f1}$) in case the neighbor cell carrier frequency is different from the carrier frequency of the reference cell (equations (2c)-(2d)). For intra-frequency measurements (equations (2a)-(2b)) any group delay bias essentially cancels when performing the time differences.

The equations (2) include the time differences of the base station transmission ($T_i - T_1$). These base station synchronization differences are often referred to as "Real Time Differences (RTD)" in OTDOA location. Hence, re-arranging equations (2) gives:

$$OTDOA_{2,1} - RTD_{2,1} = \frac{d_2 - d_1}{c} + (\varepsilon_2 - \varepsilon_1) \quad \text{(EQ 3a)}$$

$$\vdots$$

$$OTDOA_{i,1} - RTD_{i,1} = \frac{d_i - d_1}{c} + (\varepsilon_i - \varepsilon_1) \quad \text{(EQ 3b)}$$

$$OTDOA_{i+1,1} - RTD_{i+1,1} = \frac{d_{i+1} - d_1}{c} + (\Delta_{f2} - \Delta_{f1}) + (\varepsilon_{i+1} - \varepsilon_1) \quad \text{(EQ 3c)}$$

$$\vdots$$

$$OTDOA_{N,1} - RTD_{N,1} = \frac{d_N - d_1}{c} + (\Delta_{f2} - \Delta_{f1}) + (\varepsilon_N - \varepsilon_1) \quad \text{(EQ 3d)}$$

Without loss of generality, one may, for example, adopt a two dimensional Cartesian coordinate system in the x-y plane, and denote the mobile location coordinates as (x,y) and the base station i coordinates as $(x_i, y_i)$. The distances $d_i$ can then be written as:

$$d_i = \sqrt{(x-x_i)^2 + (y-y_i)^2} \quad \text{(EQ 4)}$$

and equations (3) can be expanded into:

$$OTDOA_{2,1} - RTD_{2,1} = \quad \text{(EQ 5a)}$$
$$\frac{\sqrt{(x-x_2)^2+(y-y_2)^2} - \sqrt{(x-x_1)^2+(y-y_1)^2}}{c} + (\varepsilon_2 - \varepsilon_1)$$
$$\vdots$$

$$OTDOA_{i,1} - RTD_{i,1} = \quad \text{(EQ 5b)}$$
$$\frac{\sqrt{(x-x_i)^2(y-y_i)^2} - \sqrt{(x-x_1)^2+(y-y_1)^2}}{c} + (\varepsilon_i - \varepsilon_1)$$

$$OTDOA_{i+1,1} - RTD_{i+1,1} = \quad \text{(EQ 5c)}$$
$$\frac{\sqrt{(x-x_{i+1})^2+(y-y_{i+1})^2} - \sqrt{(x-x_1)^2+(y-y_1)^2}}{c} +$$
$$(\Delta_{f2} - \Delta_{f1}) + (\varepsilon_{i+1} - \varepsilon_1)$$
$$\vdots$$

$$OTDOA_{N,1} - RTD_{N,1} = \quad \text{(EQ 5d)}$$
$$\frac{\sqrt{(x-x_N)^2+(y-y_N)^2} - \sqrt{(x-x_1)^2+(y-y_1)^2}}{c} +$$
$$(\Delta_{f2} - \Delta_{f1}) + (\varepsilon_N - \varepsilon_1)$$

For OTDOA location in certain implementations, a network may be synchronized, i.e., such that an RTD may be zero or some other known value. Assuming $RTD_{i,1}=0$, equations (5) simplify to:

$$OTDOA_{2,1} = \quad \text{(EQ 6a)}$$
$$\frac{\sqrt{(x-x_2)^2+(y-y_2)^2} - \sqrt{(x-x_1)^2+(y-y_1)^2}}{c} + (\varepsilon_2 - \varepsilon_1)$$
$$\vdots$$

$$OTDOA_{i,1} = \quad \text{(EQ 6b)}$$
$$\frac{\sqrt{(x-x_i)^2+(y-y_i)^2} - \sqrt{(x-x_1)^2+(y-y_1)^2}}{c} + (\varepsilon_i - \varepsilon_1)$$

$$OTDOA_{i+1,1} = \quad \text{(EQ 6c)}$$
$$\frac{\sqrt{(x-x_{i+1})^2+(y-y_{i+1})^2} - \sqrt{(x-x_1)^2+(y-y_1)^2}}{c} +$$
$$(\Delta_{f2} - \Delta_{f1}) + (\varepsilon_{i+1} - \varepsilon_1)$$
$$\vdots$$

$$OTDOA_{N,1} = \quad \text{(EQ 6d)}$$
$$\frac{\sqrt{(x-x_N)^2+(y-y_N)^2} - \sqrt{(x-x_1)^2+(y-y_1)^2}}{c} +$$
$$(\Delta_{f2} - \Delta_{f1}) + (\varepsilon_N - \varepsilon_1)$$

In case of no measurement errors ($\varepsilon_i=0$) the set of equations (6) contain three unknowns, namely the mobile location coordinates (x,y) and the inter-frequency bias ($\Delta_{f2}-\Delta_{f1}$). Thus, in certain instances, $OTDOA_{i,1}$ may be determined by a mobile device, and base station coordinates $(x_i, y_i)$ may be known or otherwise determinable, e.g., via various resources within the network.

The set of equations (6) may be compact written using matrix notation:

$$r = f(x,b) + n \quad \text{(EQ 7)}$$

where r is a N−1 dimensional column vector of OTDOA measurements f is a N−1 dimensional column vector containing the range differences and inter-frequency biases:

$$f_i(x,y,b) = \frac{\sqrt{(x-x_i)^2+(y-y_i)^2} - \sqrt{(x-x_1)^2+(y-y_1)^2}}{c} + b \quad \text{(EQ 8)}$$

x is the (unknown) mobile location $[x,y]^T$ b is an N−1 dimensional column vector containing the inter-frequency measurement bias $b_i = (\Delta_{f2}-\Delta_{f1}) = \Delta(f_1, f_2)$.

If the OTDOA measurement (i,1) is an intra-frequency measurement, then $b_i=0$.

n is an N−1 dimensional column vector containing the OTDOA measurement error.

If x and b are regarded as an unknown but non-random vector and n is assumed to have zero-mean and a Gaussian distribution, then a conditional probability density function of r given x and b is:

$$p(r \mid x, b) = \quad \text{(EQ 9)}$$
$$\frac{1}{(2\pi)^{(N-1)/2}|N|^{1/2}} \exp\{-(1/2)[r-f(x,b)]^T N^{-1}[r-f(x,b)]\}$$

where N is the covariance matrix of the measurement error:

$$N = E\{(n-E\{n\})(n-E\{n\})^T\} \quad \text{(EQ 10)}$$

A maximum likelihood estimator is therefore the value x,b which minimize the following cost function:

$$Q(x,b) = [r-f(x,b)]^T N^{-1} [r-f(x,b)] \quad \text{(EQ 11)}$$

Therefore, $$(\hat{x},\hat{b}) = \operatorname{argmin}\{[r-f(x,b)]^T N^{-1}[r-f(x,b)]\} \quad \text{(EQ 12)}$$

In an example embodiment, a navigation solution may be provided by way of a Taylor series estimation. For example, the function f(x,b) in equation (7) is a non-linear vector function. Thus, one approach to minimize the cost function (11) is to linearize f(x,b). For example, f(x,b) can be expanded in a Taylor series estimation about a reference point $(x_0, b_0)$ and the second and higher terms can be neglected. Defining the vector of unknowns z=[x, b]=(x, y, $\Delta(f_1, f_2)$)=(x, y, b), the function f(z) may be represented as:
as:

$$f(z) \approx f(z_0) + G \cdot (z-z_0) \quad \text{(EQ 13)}$$

where, $$G = \begin{bmatrix} \frac{\partial f_2}{\partial x}\big|_{z=z_0} & \frac{\partial f_2}{\partial y}\big|_{z=z_0} & \frac{\partial f_2}{\partial b}\big|_{z=z_0} \\ \frac{\partial f_3}{\partial x}\big|_{z=z_0} & \frac{\partial f_3}{\partial y}\big|_{z=z_0} & \frac{\partial f_3}{\partial b}\big|_{z=z_0} \\ \vdots & \vdots & \vdots \\ \frac{\partial f_N}{\partial x}\big|_{z=z_0} & \frac{\partial f_N}{\partial y}\big|_{z=z_0} & \frac{\partial f_N}{\partial b}\big|_{z=z_0} \end{bmatrix} \quad (EQ\ 14)$$

Accordingly, in certain implementations, one may assume that $z_0$ is close enough to $z$ that the linearization in (13) is an accurate approximation. Combining (11) and (13) gives:

$$Q(z) = [r_1 - Gz]^T N^{-1} [r_1 - Gz] \quad (EQ\ 15)$$

with $$r_1 = r - f(z_0) + G z_0 \quad (EQ\ 16)$$

To minimize Q, one may calculate:

$$\nabla_z Q(z) = \left[ \frac{\partial Q}{\partial x}, \frac{\partial Q}{\partial y}, \frac{\partial Q}{\partial b} \right]^T \quad (EQ\ 17)$$

and solve for z such that $\nabla_z Q(z) = 0$. Therefore, $$\begin{aligned} \nabla_z Q(z) &= 2(\nabla_z (r_1 - Gz)^T) N^{-1} (r_1 - Gz) \\ &= 2(G^T N^{-1} Gz - G^T N^{-1} r_1) \end{aligned} \quad (EQ\ 18)$$

Now one may set $$\nabla_z Q(z)\big|_{z=\hat{z}} = 2(G^T N^{-1} G\hat{z} - G^T N^{-1} r_1) = 0 \quad (EQ\ 19)$$

Assuming $G^T N^{-1} G$ is nonsingular, one may obtain:

$$\hat{z} = (G^T N^{-1} G)^{-1} G^T N^{-1} r_1 \quad (EQ\ 20)$$

Substituting (16) into (20) gives $$\hat{z} = z_0 + (G^T N^{-1} G)^{-1} G^T N^{-1} (r - f(z_0)) \quad (EQ\ 21)$$

Equation (21) gives the desired estimate of the mobile location together with the inter-frequency bias compensation. The matrix G is given by equation (14), and with (8) the partial derivatives are $$G = \begin{bmatrix} \frac{x-x_2}{d_2} - \frac{x-x_1}{d_1}, & \frac{y-y_2}{d_2} - \frac{y-y_1}{d_1}, & 0\,|\,1 \\ \frac{x-x_3}{d_3} - \frac{x-x_1}{d_1}, & \frac{y-y_3}{d_3} - \frac{y-y_1}{d_1}, & 0\,|\,1 \\ \vdots & \vdots & \vdots \\ \frac{x-x_N}{d_N} - \frac{x-x_1}{d_1}, & \frac{y-y_N}{d_N} - \frac{y-y_1}{d_1}, & 0\,|\,1 \end{bmatrix} \quad (EQ\ 22)$$

The last column in G contains either a zero or a one value. It is 0, if the measurement $OTDOA_{i1}$ is an intra-frequency measurement and 1 if the measurement $OTDOA_{i1}$ is an inter-frequency measurement.

The equation (21) describes an iterative procedure to estimate the mobile device location together with the inter-frequency bias compensation. The starting point $z_0 = (x_0, y_0, b_0)$ may be chosen with the help of the Cell-ID location or the like of the mobile device, and $b_0$ may be set to 0. With this initial guess, the mobile device position and inter-frequency bias compensation $\hat{z}$ may be calculated according to (21). At the next step, this estimated position and inter-frequency bias compensation $\hat{z}$ may be used as a new initial guess. The iterations will have converged when the change in the estimated position is essentially zero.

The above exemplary procedure assumes TOA measurements on two carrier frequencies. However, the described procedure is not limited to two carrier frequencies. Skilled artisans may extend the procedure to (for example) three carrier frequencies by (for example) adding a fourth column to the G matrix in equation 22, describing the inter-frequency bias compensation between another pair of frequencies.

Figure 3:
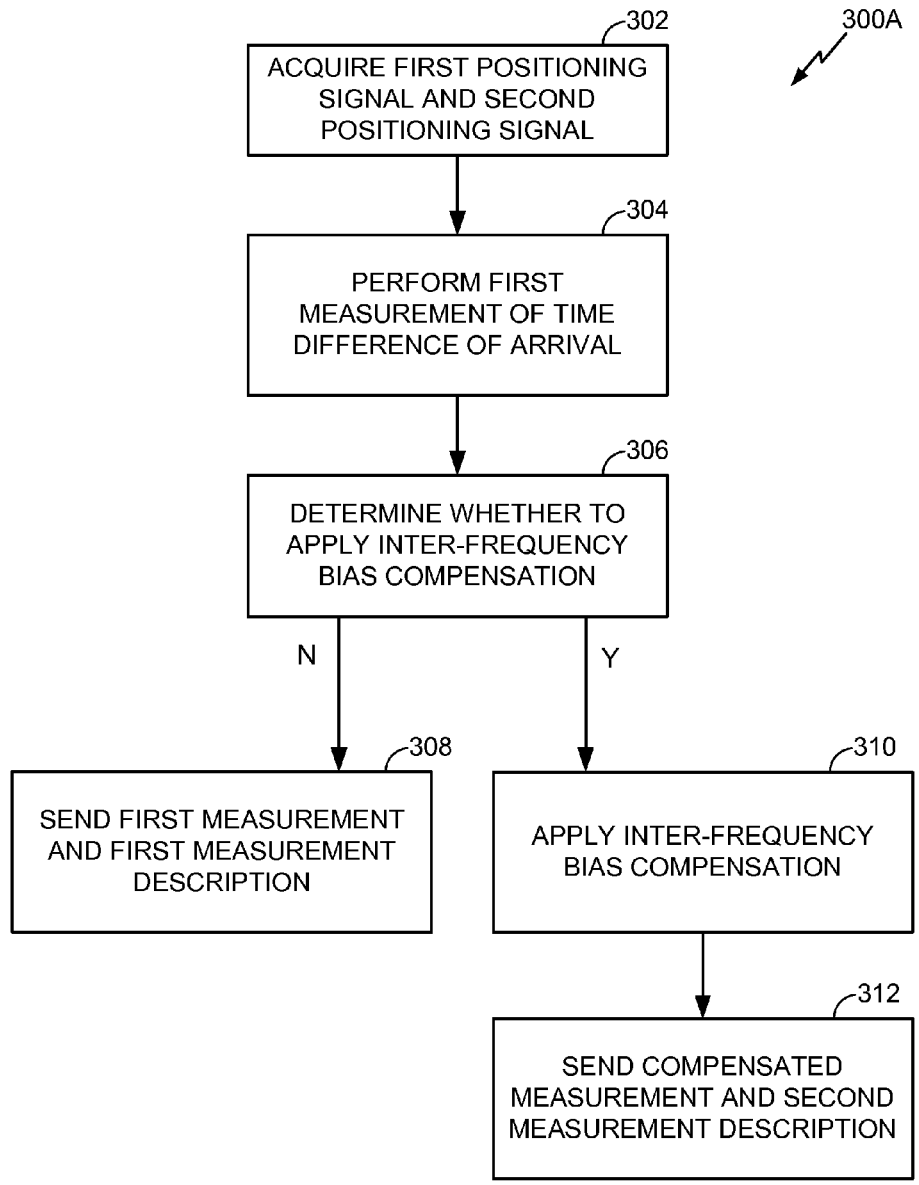
FIG. 3 is a flowchart illustrating an example process, by a mobile device, of determining a position of the mobile device, in accordance with an example implementation.

FIG. 3 is a flowchart illustrating an example process 300A for use in a mobile device to determine, at least in part, a position of a mobile device (e.g., mobile device 136 of FIG. 1, and/or mobile device 200 of FIG. 2). At process block 302, mobile device may acquire a first positioning signal (e.g., positioning signal 202) and a second positioning signal (e.g., positioning signal 204). In one aspect, the mobile device acquires the first and second positioning signals in response to assistance data 102 provided by server 146. The assistance data 102 may include relevant information (e.g., carrier frequencies) of the positioning signals that are to be used by the mobile device for determining one or more OTDOA measurements. Thus, in one example, the assistance data may correspond to (first) positioning signal 202 transmitted by a (first) base station 206 and to a (second) positioning signal 204 transmitted by a (second) base station 208, where the first positioning signal is transmitted on a first frequency (e.g., F1) and the second positioning signal is transmitted on a second frequency (e.g., F2) that is separate and distinct from the first frequency (e.g., F1≠F2).

At process block 304, the mobile device may perform a first measurement of a time difference of arrival of the pair of first and second positioning signals. In one example, performing the first measurement includes performing an Observed Time Difference of Arrival (OTDOA) measurement of the first and second positioning signals. At process block 304, the first measurement is uncompensated for any inter-frequency related delays (e.g., group delay) corresponding to the first frequency (e.g., F1), the second frequency (e.g., F2), or both the first and second frequencies (e.g., F1 and F2). Thus, any initial RSTD determinations made by the mobile device at process block 304 do not include inter-frequency bias compensation for a difference between the first frequency of the first positioning signal and the second frequency of the second positioning signal, and thus are not compensated for different group delays that may be encountered by the first and/or second positioning signals.

Figure 4:
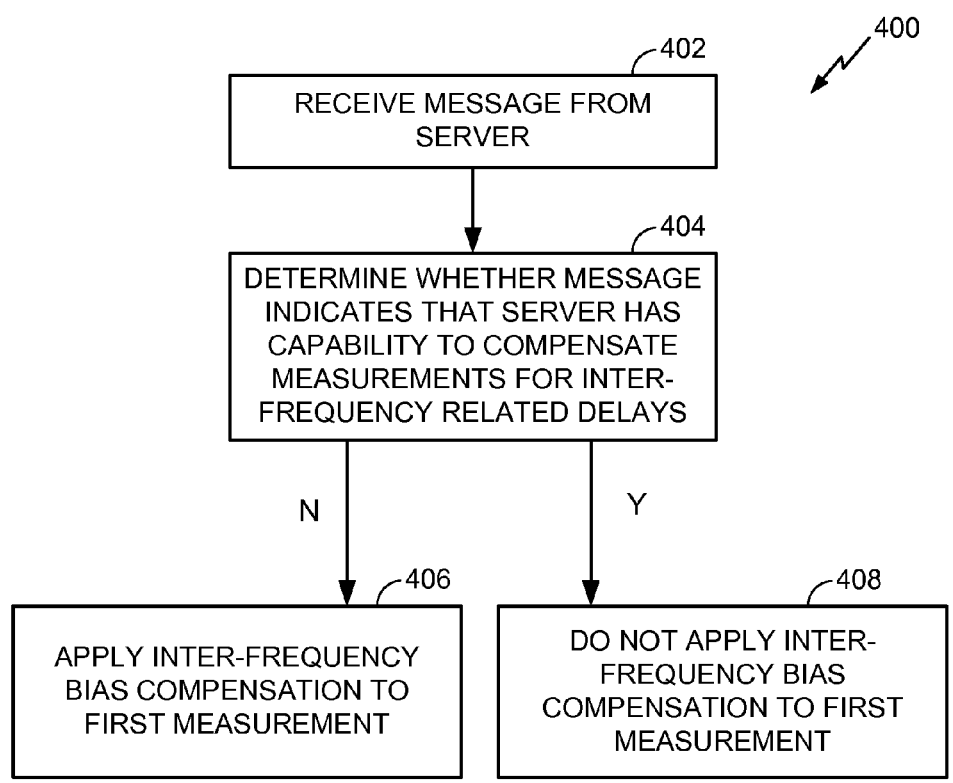
FIG. 4 is a flowchart illustrating an example process of determining whether to apply an inter-frequency bias compensation at the mobile device, in accordance with an example implementation.

In process block 306, a determination is made as to whether or not to apply an inter-frequency bias compensation to the first measurement at the mobile device. In certain implementations, the mobile device may selectively determine whether or not to apply some form of inter-frequency bias compensation based on one or more factors, such as, just to name a few examples, one or more of the first or second positioning signals, one or more of the capabilities, resources, of the mobile device and/or server, or other pertinent information available with regard to the mobile device, the server, the network, or some combination thereof. By way of example, the determination of whether or not to apply the inter-frequency bias compensation to the first measurement at the mobile device may be based on a known, or dynamically determined, capability of a server (e.g., location server 146) to compensate for the inter-frequency related delays at the server. FIG. 4 is a flowchart illustrating an example process 400 of determining whether to apply an inter-frequency bias compensation at the mobile device, in accordance with such an example implementation. In the illustrated example, process block 402 includes the mobile device receiving a message from the server (e.g., server 146). In one embodiment, the message received at the mobile device is an LTE Positioning Protocol (LPP) message that indicates whether the server includes the capability to compensate measurements at the server for the inter-frequency related delays. Upon receiving the message from the server, the mobile device may then, in process block 404, determine whether the message indicates that the server does indeed have the capability to compensate measurements for the inter-frequency related delays. If the message received from the server indicates that the server does have the capability to compensate measurements for the inter-frequency related delays, process block 408 includes determining to not apply an inter-frequency bias compensation to the first measurement and process 300 (see FIG. 3) proceeds to process block 308, where the mobile device sends the first (i.e., uncompensated) measurement to the server. In one aspect, as shown in process block 308, the mobile device may send, in addition to the first measurement, a first measurement description to the server. The first measurement description may indicate, among other things, that the first measurement has not been compensated at the mobile device for the inter-frequency related delays (e.g., mobile device has not applied an inter-frequency bias compensation to the first measurement). In one embodiment, sending the first measurement description to the server includes sending an LTE Positioning Protocol (LPP) message. The LPP message may include a flag, where the logic state of the flag indicates whether the corresponding first measurement has been compensated for the inter-frequency related delays. As will be described in more detail below, the server (e.g., server 146) may then determine the inter-frequency bias compensation of the first measurement at the server and determine, at least, the position of the mobile device.

Returning now to FIG. 4, if the message received from the server in process block 402 indicates that the server does not have the capability to compensate measurements for the inter-frequency related delays, process block 406 includes determining to apply the inter-frequency bias compensation to the first measurement at the mobile device, itself. Thus, if so, process 300 (see FIG. 3) proceeds to process block 310, where the mobile device applies an inter-frequency bias compensation to the first measurement to generate a compensated measurement. In one example, applying the inter-frequency bias compensation to the first measurement at the mobile device includes determining a value of the inter-frequency bias compensation. In certain implementations a mobile device may include a calibration table or other mechanism corresponding to inter-frequency bias compensations for the first and second frequencies that may be applied on an RSTD determination made by the mobile device at process block 310. In another implementation, the mobile device may (dynamically) calculate an inter-frequency bias compensation at process block 310. That is, the mobile device may correct or otherwise adjust the first measurement for inter-frequency related delays based on a calculated inter-frequency bias compensation, by performing an iterative procedure, such as equation 21, described above to provide an estimated position of the mobile device and the inter-frequency bias compensation. In certain example implementations, the mobile device may be optionally configured to store locally (i.e., at the mobile device) one or more determined inter-frequency bias compensations for use in future RSTD measurements, e.g., to potentially enable the mobile device to update and maintain a more accurate calibration table or other like capability over time.

In process block 312, the mobile device then sends the compensated measurement to the server, where the server may determine a position of the mobile device based on the compensated measurement. Similar to process block 308, described above, the mobile device may send, in addition to the compensated measurement, a second measurement description to the server. The second measurement description may indicate, among other things, that the compensated measurement has been compensated at the mobile device for the inter-frequency related delays (e.g., mobile device has applied an inter-frequency bias compensation to the first measurement). In one embodiment, sending the second measurement description to the server includes sending an LTE Positioning Protocol (LPP) message. The LPP message may include a flag, where the logic state of the flag indicates whether the corresponding first measurement has been compensated for the inter-frequency related delays. As will be described in more detail below, the server (e.g., server 146) may then determine the position of the mobile device based on the compensated measurement.

In certain aspects, the second measurement description may include further information to aide or otherwise be utilized by the server in determining the position of the mobile device. For example, the second measurement description may further include information indicating a value of the inter-frequency bias compensation that was applied by the mobile device to the first measurement in process block 310. In another implementation, the second measurement description may further include a type of the inter-frequency bias compensation that was applied by the mobile device to the first measurement in process block 310. By way of example, the second measurement description may indicate that the inter-frequency bias compensation applied by the mobile device was a type that was retrieved from a calibration table (discussed above), or was of a type that was dynamically calculated (e.g., by way of equation 21). In another implementation, the second measurement description may further include a metric, determined by the mobile device, which indicates a reliability or accuracy of the inter-frequency bias compensation applied to the first measurement in process block 310. In yet another implementation, the second measurement description indicates an age of the inter-frequency bias compensation that was applied by the mobile device in process block 310. That is, the age may be indicative of a time that the inter-frequency bias compensation was entered into a calibration table and/or a time that the inter-frequency bias compensation was dynamically calculated by the mobile device. In a further implementation, the second measurement description may include at least a portion of data used by the mobile device to perform the first measurement of the time difference of arrival. For example, the portion of data used, by the mobile device, to perform the first measurement may include a time of arrival (e.g., timestamp) of the first positioning signal, and/or a time of arrival (e.g., timestamp) of the second positioning signal acquired in process block 302.

Figure 5:
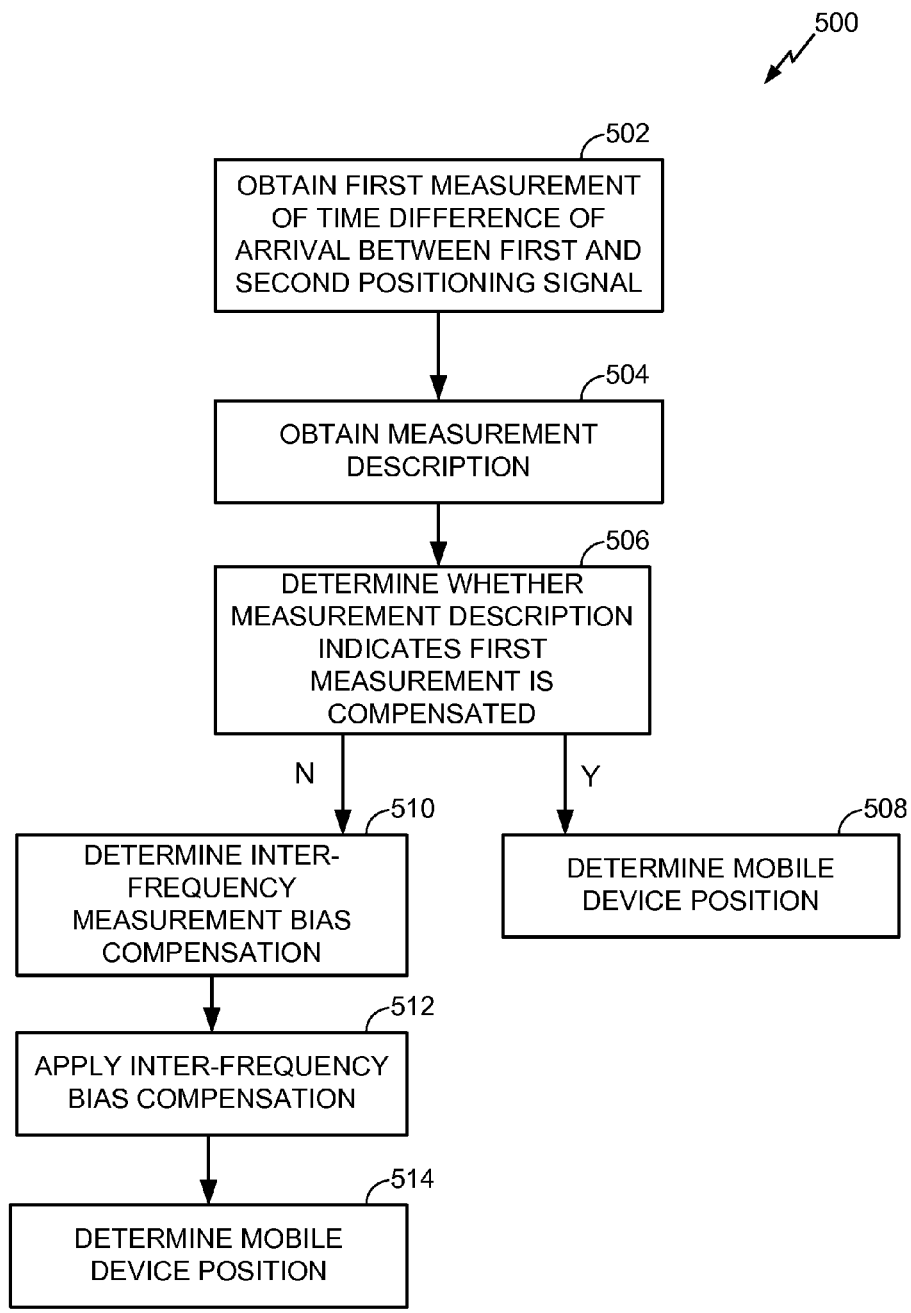
FIG. 5 is a flowchart illustrating an example process, by a server, of determining a position of the mobile device, in accordance with an example implementation.

FIG. 5 is a flowchart illustrating an example process 500 for use by a server (e.g., server 146), of determining a position of the mobile device, in accordance with an example implementation. At process block 502, a server may obtain a first measurement of a time difference of arrival between a first positioning signal and a second positioning signal, as determined by a mobile device (e.g., mobile device 136 and/or 200). As discussed above, the first positioning signal corresponds to a positioning signal 202 that was transmitted on a first frequency (e.g., F1) and the second positioning signal corresponds to a positioning signal 204 that was transmitted on a second frequency (e.g., F2) that is separate and distinct from the first frequency (e.g., F1≠F2).

In process block 504, the server then obtains a measurement description that corresponds to the first measurement obtained in process block 502. The measurement description may indicate, among other things, whether or not the first measurement has been compensated at the mobile device for the inter-frequency related delays (e.g., whether the mobile device has applied an inter-frequency bias compensation to the first measurement). In one embodiment, obtaining the measurement description at the server includes receiving an LTE Positioning Protocol (LPP) message. As discussed above, the LPP message may include a flag, where the logic state of the flag indicates whether the corresponding first measurement has been compensated for the inter-frequency related delays. Thus, process block 506 includes determining whether the measurement description received at the server indicates that the first measurement has been compensated, by the mobile device, for inter-frequency related delays corresponding to the first frequency (e.g., F1), the second frequency (e.g., F2), or both the first frequency and the second frequency.

If the measurement description obtained by the server in process block 504 indicates that the first measurement has not been compensated by the mobile device for the inter-frequency related delays, then process 500 proceeds to process block 510, where the server determines a value of an inter-frequency bias compensation to be applied to the first measurement at the server, itself. In certain implementations a server may include a calibration table or other mechanism corresponding to inter-frequency bias compensations for the first and second frequencies that may be applied on an RSTD determination (e.g., the first measurement) made by the mobile device. For example, the server may recognize the particular mobile device via an International Mobile Station Equipment Identity (IMEI) or any other identity which uniquely identifies the mobile device's hardware, which may be included in the measurement description or otherwise provided by the mobile device to the server. The location server may have previously determined the inter-frequency bias compensation value for this particular mobile device and may have stored this value in a calibration table at the server. In another implementation, the server may (dynamically) calculate an inter-frequency bias compensation at process block 510. That is, the server may correct or otherwise adjust the first measurement for inter-frequency related delays based on a calculated inter-frequency bias compensation. Process 500 then proceeds to process block 512, where the server applies the inter-frequency bias compensation to the first measurement to generate a compensated measurement and then determines a position of the mobile device based on the compensated measurement (i.e., process block 514). In one embodiment, process blocks 510, 512, and 514, combined, are embodied by the iterative procedure described above with reference to equation 21 that provides the inter-frequency bias compensation as well as the position of the mobile device based on the first (uncompensated) measurement.

Returning now to process block 506, if the measurement description obtained by the server in process block 504 indicates that the first measurement has been compensated by the mobile device for the inter-frequency related delays, then process 500 proceeds to process block 508, where the server determines a position of the mobile device based on the first (compensated) measurement. Thus, in one example, the server may determine the position of the mobile device based on the first (compensated) measurement without determining an inter-frequency bias compensation at the server.

However, in certain implementations, the server may decide to determine a new inter-frequency bias compensation at the server, even if the measurement description indicates that the first measurement has already been compensated by the mobile device. For example, as mentioned above, the measurement description received by the server may include additional information, beyond just indicating whether the first measurement has been compensated for the inter-frequency related delays. In certain implementations the measurement description may further include a type of the inter-frequency bias compensation that was applied by the mobile device to the first measurement. By way of example, the measurement description may indicate that the inter-frequency bias compensation applied by the mobile device was of a type that was retrieved from a calibration table (discussed above), or was of a type that was dynamically calculated (e.g., by way of equation 21). In this example, the server may decide to determine a new inter-frequency bias compensation if the measurement description indicates that the inter-frequency bias compensation applied by the mobile device was of the type retrieved from a calibration table, but may decide to not determine a new inter-frequency bias compensation if the mobile device applied inter-frequency bias compensation was of the type dynamically calculated by the mobile device.

In another implementation, the measurement description may further include a metric, determined by the mobile device, which indicates a reliability or accuracy of the inter-frequency bias compensation applied to the first measurement by the mobile device. In this example, the server may decide to determine a new inter-frequency bias compensation if the metric indicates that the reliability or accuracy of inter-frequency bias compensation applied by the mobile device is below a reliability/accuracy threshold, but not if the metric is at or above the reliability/accuracy threshold.

In yet another implementation, the measurement description indicates an age of the inter-frequency bias compensation that was applied by the mobile device. That is, the age may be indicative of a time that the inter-frequency bias compensation was entered into a calibration table at the mobile device and/or a time that the inter-frequency bias compensation was dynamically calculated by the mobile device. In this example, the server may decide to determine a new inter-frequency bias compensation if the age of inter-frequency bias compensation applied by the mobile device is greater than an age threshold (indicating that the inter-frequency bias compensation may be stale), but not if the age is less than the age threshold (indicating that the inter-frequency bias compensation is likely fresh). In another example, the server may compare the age of the inter-frequency bias compensation applied by the mobile device with an age of an inter-frequency bias compensation previously determined by the server, where the server may apply the more recent of the two inter-frequency bias compensations.

In a further implementation, the measurement description may include at least a portion of data used by the mobile device to perform the first measurement of the time difference of arrival. For example, the portion of data used, by the mobile device, to perform the first measurement may include a time of arrival (e.g., timestamp) of the first positioning signal, and/or a time of arrival (e.g., timestamp) of the second positioning signal acquired by the mobile device. Thus, process blocks 508 and/or 514, of determining the position of the mobile device, may include determining the RSTD calculation at the server, based on the data included in the measurement description.

Figure 6:
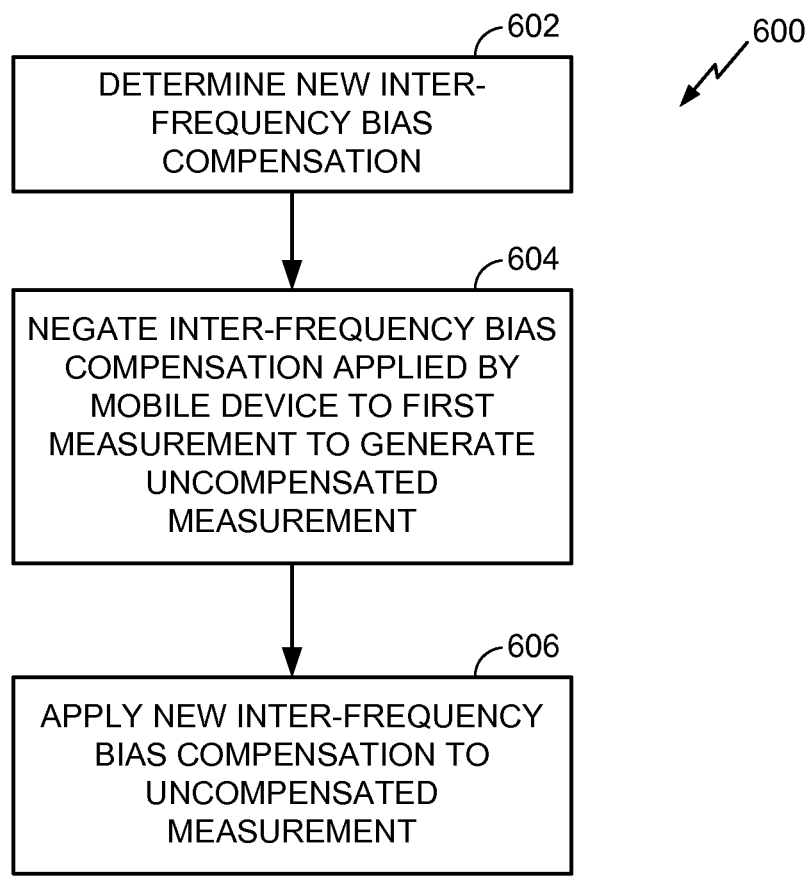
FIG. 6 is a flowchart illustrating an example process, by a server, of determining a position of the mobile device that includes determining a new inter-frequency bias compensation by the server, in accordance with an example implementation.

FIG. 6 is a flowchart illustrating an example process 600 for use by a server of determining a position of the mobile device that includes determining a new inter-frequency bias compensation by the server, in accordance with an example implementation. In other words, a server, in accordance with the teachings herein, may reverse or otherwise negate an inter-frequency bias compensation applied by the mobile device. As described above, in some implementations, the decision to determine a new inter-frequency bias compensation may be based on information included in the received measurement description. Furthermore, the determination of a value of the new inter-frequency bias compensation may be based, at least in part on information included in the measurement description. Thus, process 600 is one possible implementation of process block 508 of FIG. 5.

In process block 602, the server may determine a new inter-frequency bias compensation for compensating for inter-frequency related delays corresponding to the first frequency, the second frequency, or both the first and second frequency of the positioning signals used by the mobile device is performing the OTDOA measurements. In certain implementations, the new inter-frequency bias compensation may be determined by the server by way of a look-up table and/or may be dynamically calculated at the server by way of an algorithm/equation, such as the iterative procedure described above with reference to equation 21. Next, in process block 604, the server negates the inter-frequency bias compensation that was applied by the mobile device to the first measurement in order to generate an uncompensated measurement. For example, if a mobile device provides the value of the applied inter-frequency bias compensation used for compensating a determined OTDOA measurement, the server may reverse this compensation to obtain uncompensated OTDOA measurements, and then apply the procedure as if the mobile device would have provided uncompensated OTDOA measurements. By way of example, the measurement description received at the server in process block 504 may further include information indicating a value of the inter-frequency bias compensation that was applied by the mobile device to the first measurement. Thus, the server may utilize this value provided in the measurement description to remove the inter-frequency bias compensation that was applied by the mobile device to generate the uncompensated measurement. Next, in process block 606, the server applies the new inter-frequency bias compensation to the uncompensated measurement, such that the server may determine the position of the mobile device.

In one aspect, process blocks 602, 604, and 606, combined, may be embodied by the iterative procedure described above with reference to equation 21 that provides the inter-frequency bias compensation as well as the position of the mobile device based on a compensated first measurement. Thus, in one example, the server does not need to reverse any inter-frequency bias compensation made by the mobile device. Utilizing the iterative procedure of equation 21, the server calculation would provide a new inter-frequency bias compensation between the first and second positioning signals, whatever this bias is (e.g., the new inter-frequency bias compensation is calculated to compensate for both the mobile device applied inter-frequency bias compensation plus the actual inter-frequency bias).

Figure 7:
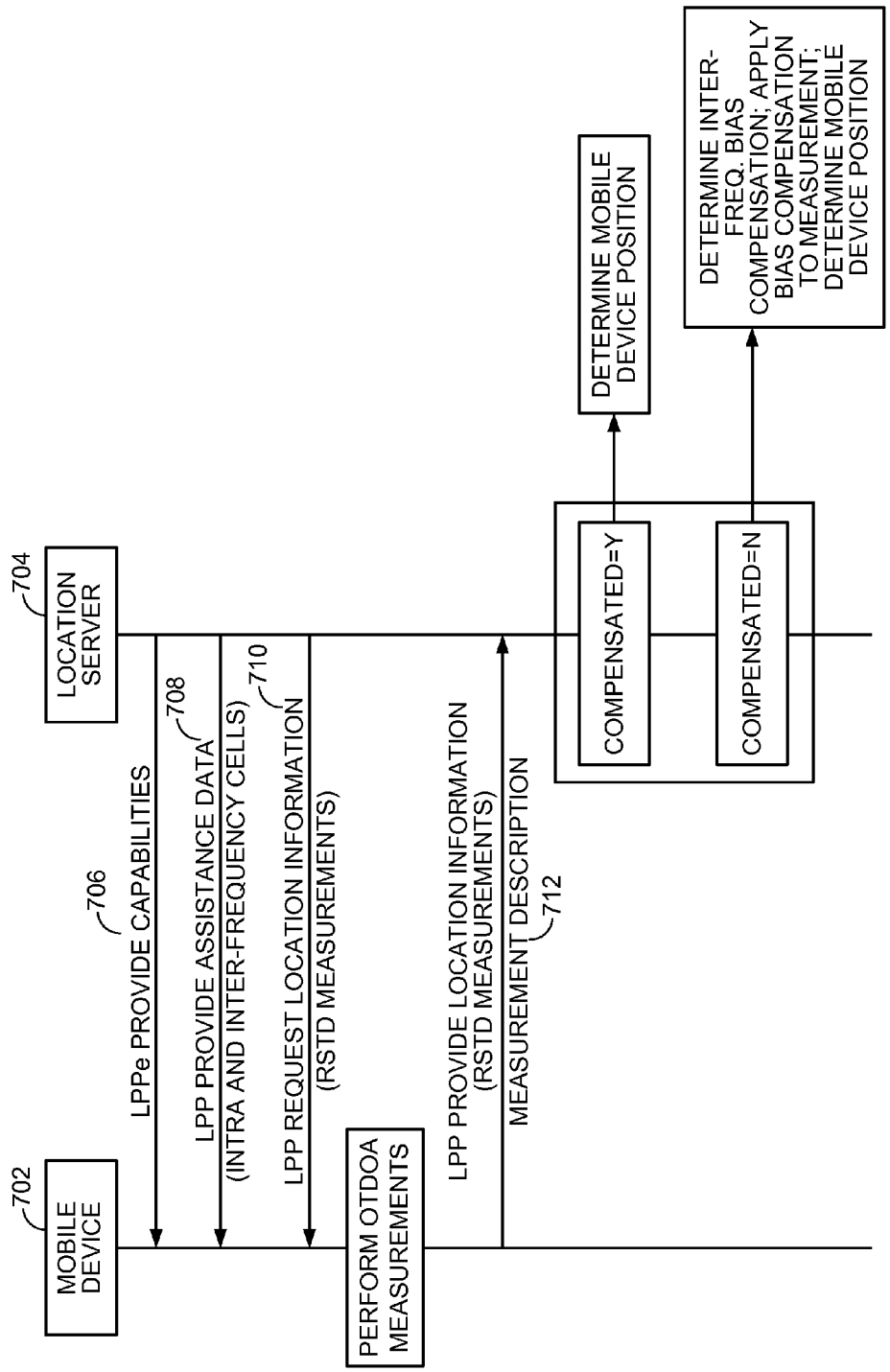
FIG. 7 is a diagram illustrating an example message flow for use in determining a position of a mobile device, in accordance with an example implementation.

FIG. 7 is a diagram illustrating message flow for use, at least in part, in determining a position of a mobile device (e.g., such as mobile device 136 in FIG. 1). The example message flow illustrated in FIG. 7 corresponds to the processes 300, 400, 500, and 600 for FIGS. 3, 4, 5, and 6, respectively. As shown, the message flow illustrated in FIG. 7 includes the example feature of the location server 704 indicating to the mobile device 702 whether the location server 704 has a capability of compensating, at the location server 704, measurements of inter-frequency related delays. For example, if location server 704 is configured to perform a process of determining the inter-frequency bias compensation, location server 704 may indicate such to the mobile device 702 via a message, such as an LPPe PROVIDE CAPABILITIES message 706. However, in certain other implementations, location server 704 may not need to indicate such capabilities to mobile device 702. That is, mobile device 702 may perform either compensated or uncompensated RSTD measurements, for example, possibly based on certain indicated or already known capabilities of location server 704. That is, if location server 704 has a capability to determine inter-frequency bias compensation, then mobile device 702 may determine applicable OTDOA measurements and possibly indicate such in a resultant measurement description 712 sent to location server 704. Other already available capabilities may also be indicated in the LPPe PROVIDE CAPABILITIES message 706, such as, for example, whether the location server 704 supports OTDOA positioning, GNSS, assistance data, etc. For example, in one implementation, mobile device 702 would not need to request GNSS assistance data if the location server 704 does not support GNSS.

In one example, location server 704 provides the LPPe PROVIDE CAPABILITIES message 706 when the location server 704 starts a location session. In certain operations, the location server 704 may receive a request for the mobile device position (i.e., location) from another entity (e.g., from an emergency center (PSAP)) and in response thereto initiate a location session by sending the LPPe PROVIDE CAPABILITIES message 706 to the mobile device 702.

Also shown in FIG. 7, is the location server 704 sending an LPP PROVIDE ASSISTANCE DATA message 708 to the mobile device 702. The LPP PROVIDE ASSISTANCE DATA message 708 may include relevant information (e.g., carrier frequencies) of the positioning signals that are to be used by the mobile device for determining one or more OTDOA measurements. Thus, in one example, the LPP PROVIDE ASSISTANCE DATA message 708 may correspond to (first) positioning signal 202 transmitted by a (first cell) base station 206 and to a (second) positioning signal 204 transmitted by a (second cell) base station 208, where the first positioning signal is transmitted on a first frequency (e.g., F1) and the second positioning signal is transmitted on a second frequency (e.g., F2) that is separate and distinct from the first frequency (e.g., F1≠F2).

In certain implementations, the LPP PROVIDE ASSISTANCE DATA message 708 may include one or more of a neighbor cell list the mobile device 702 should use for the RSTD measurements, and information required to enable the mobile device 702 to make the measurements (e.g., the carrier frequency, bandwidth, the cell ID, the PRS configuration information, and/or a search window (which tells the mobile device 702 in which time interval the mobile device is expected to measure the RSTD)).

Also shown in FIG. 7, is the location server 704 sending an LPP REQUEST LOCATION INFORMATION message 710 to the mobile device 702. The LPP REQUEST LOCATION INFORMATION message 710 requests RSTD measurements from the mobile device 702, and may also specify a response time (i.e., when the mobile device 702 should report the measurements, or in other words, how long the mobile device 702 has to make the measurements).

Figure 8:
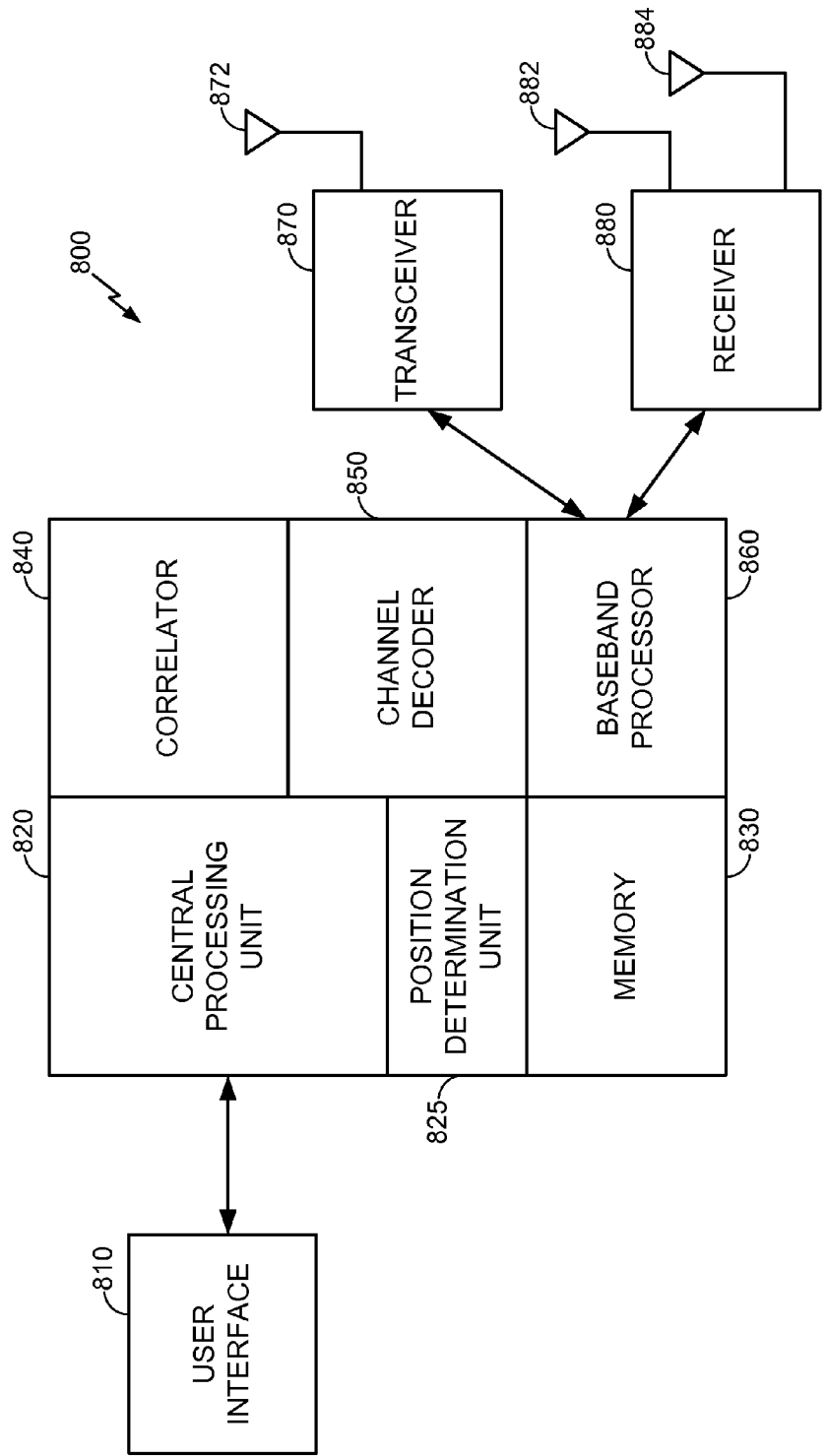
FIG. 8 is a functional block diagram showing certain features of an example mobile device, in accordance with an example implementation.

FIG. 8 is a block diagram of an example of mobile device 800 configured to perform or otherwise support any of the example applicable techniques described herein. Additionally, mobile device 800 is one possible implementation of mobile device 136 of FIG. 1, mobile device 200 of FIG. 2, or mobile device 702 of FIG. 7.

One or more transceivers 870 may be configured to modulate an RF carrier signal with baseband information, such as voice or data, onto an RF carrier, and demodulate a modulated RF carrier to obtain such baseband information. An antenna 872 may be configured to transmit a modulated RF carrier over a wireless communication link and receive a modulated RF carrier over a wireless communication link. In one embodiment, antenna 872 may be configured to transmit cellular timing information and/or assistance data requests to a base station (e.g., base station 140-4 of FIG. 1) and receive assistance data from a base station.

A baseband processor 860 may be configured to provide baseband information from a central processing unit (CPU) 820 to the transceiver 870 for transmission over a wireless communication link. Here, the CPU 820 may obtain such baseband information from an input device within a user interface 810. The baseband processor 860 may also be configured to provide baseband information from the transceiver 870 to the CPU 820 for transmission through an output device within the user interface 810.

The user interface 810 may comprise one or more devices for inputting or outputting user information such as voice or data. Such devices may include, by way of non-limiting examples, a keyboard, a display screen, a microphone, and a speaker.

A receiver 880 may be configured to receive and demodulate transmissions from an SPS via one or more antennas 882 and 884, and provide demodulated information to correlator 840. Correlator 840 may be configured to derive correlation functions from the information provided by receiver 880. Correlator 840 may be configured to derive pilot-related correlation functions from information relating to pilot signals provided by the transceiver 870. This information may be used by the mobile device to acquire wireless communication services. A channel decoder 850 may be configured to decode channel symbols received from baseband processor 860 into underlying source bits. In one example, where channel symbols comprise convolutionally encoded symbols, channel decoder 850 may comprise a Viterbi decoder. In a second example, where channel symbols comprise serial or parallel concatenations of convolutional codes, channel decoder 850 may comprise a turbo decoder.

A memory 830 may be configured to store machine-readable instructions which are executable to perform one or more of processes, implementations, or examples thereof which are described or suggested herein. The CPU 820 and/or the baseband processor 860 may be configured to access and execute such machine-readable instructions.

Mobile device 800 may include a position determination unit 825 that may be configured to perform positioning signal measurements and/or assistance data processing. In one example, the position determination unit 825 may be configured to generate assistance data requests and to initiate transmission of such request(s) to a base station via the transceiver 870. In another example, position determination unit 825 may process assistance data received via transceiver 870. In yet another example position determination unit 825 may perform measurements of positioning signals with or without inter-frequency bias compensation. Position determination unit 825 and the baseband processor 860 are illustrated separately for clarity, but may be a single unit. Indeed, it should be clear that, in certain implementations, all or part of one or more of the example features illustrated in FIG. 8 may be combined or otherwise share common components, etc.

The CPU 820, as well as one or more of position determination unit 825, correlator 840, channel decoder 850, and baseband processor 860 can, but need not necessarily include, one or more microprocessors, embedded processors, controllers, application specific integrated circuits (ASICs), advanced digital signal processors (ADSPs), and the like. The term processor describes the functions implemented by the system rather than specific hardware. Moreover, as used herein the term "memory" refers to any type of computer storage medium, including long term, short term, or other memory associated with mobile device 800, and is not to be limited to any particular type of memory or number of memories, or type of media upon which memory is stored.

In various embodiments, the mobile device 800 may include means for assisting in the determination of a position of the mobile device 800. For example, the mobile device 800 may include means for acquiring a first positioning signal transmitted at a first frequency and a second positioning signal transmitted at a second frequency (e.g., transceiver 870); means for performing a first measurement of a time difference of arrival between the first and second positioning signals (e.g., position determination unit 825, etc.); and means for sending the first measurement and a first measurement description to a server (e.g., transceiver 870, CPU 820, position determination unit 825, and/or memory 830).

Figure 9:
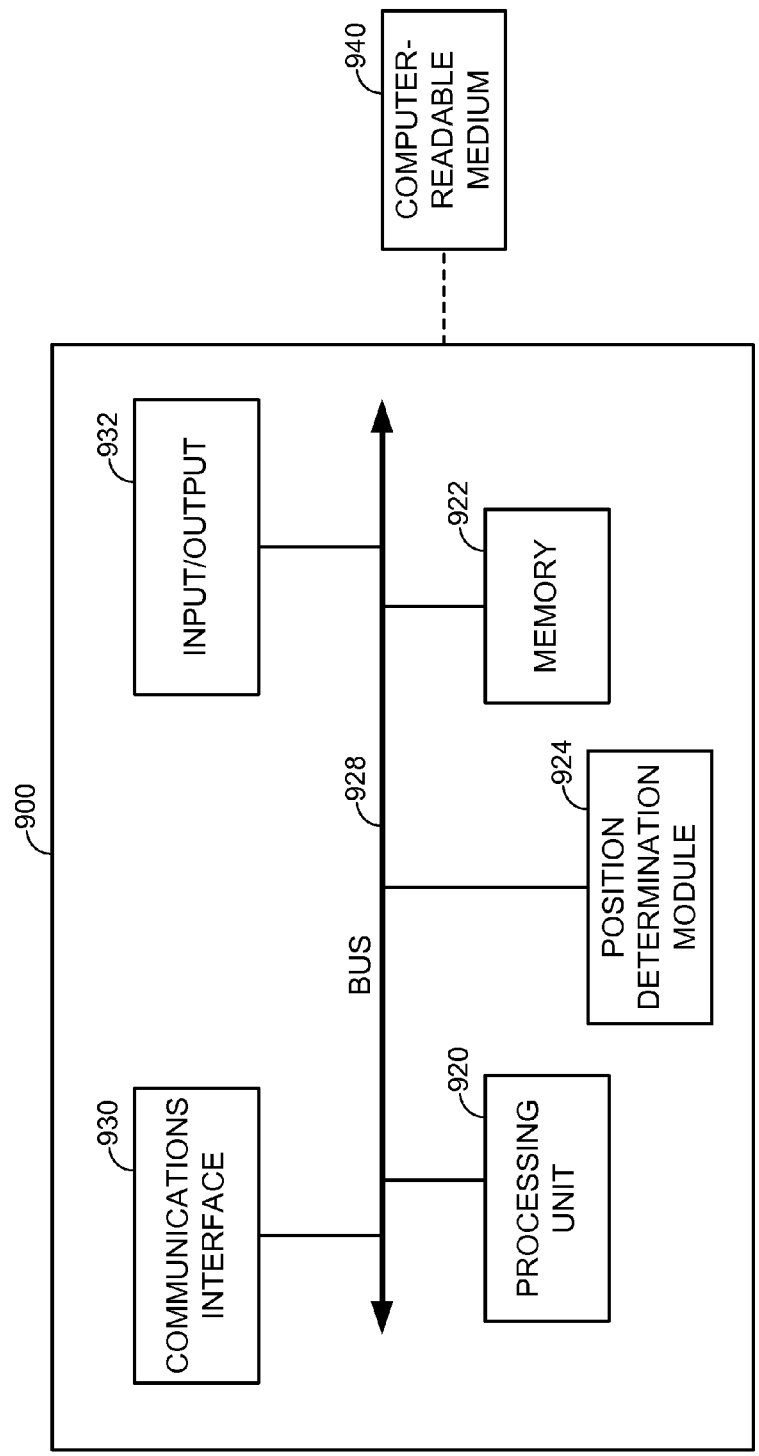
FIG. 9 is a functional block diagram showing certain features of an example server or other like computing platform/device, in accordance with an example implementation.

FIG. 9 is a functional block diagram of a (location) server 900 configurable to implement or otherwise support applicable various exemplary techniques and/or processes are described herein. For example, server 900 may be configured to perform any of the processes described in connection with the process 500 of FIG. 5 and the process 600 of FIG. 6. Server 900 represents certain exemplary features that may be provided in a possible implementation of server 146 of FIG. 1 and/or location server 704 of FIG. 7.

In the illustrated example of FIG. 9, (location) server 900 may include a position determination unit 924. Position determination unit 924 may provide position determination services for a mobile device. For example, based on received cell timing information (e.g., first measurement), measured by a mobile device (e.g., mobile device 136, 800), position determination unit 924 may determine, at least in part, an estimated position of the mobile device, e.g., with reference to some coordinate system, etc. In one example, position determination unit 924 may use one or more determined OTDOA measurements received from a mobile device and which may not include inter-frequency bias compensation for a difference between the reference signal frequencies in order to calculate the inter-frequency bias compensation and/or position. As described herein by way of various examples, position determination unit 924 may correct or otherwise adjust such determined OTDOA measurement(s) for inter-frequency measurement bias for use in determining a position of the mobile device.

Server 900 may include: one or more computing devices and/or platforms, such as, e.g., a desktop computer, a laptop computer, a workstation, a server device, or the like; one or more personal computing or communication devices or appliances, such as, e.g., a personal digital assistant, mobile communication device, or the like; a computing system and/or associated service provider capability, such as, e.g., a database or data storage service provider/system, a network service provider/system, an Internet or intranet service provider/system, a portal and/or search engine service provider/system, a wireless communication service provider/system; and/or any combination thereof.

It should be recognized that all or part of the various devices and networks shown in the examples presented herein, and the processes and methods as further described herein, may be implemented, at least in part, using or otherwise including hardware and/or firmware, possibly in combination with software (implementable instructions, etc.).

Thus, by way of example but not limitation, server 900 may include at least one processing unit 920 that is operatively coupled to a memory 922 through a bus 928. Processing unit 920 may be representative of one or more circuits configurable to perform at least a portion of a data computing procedure or process. By way of example but not limitation, processing unit 920 may include one or more processors, controllers, microprocessors, microcontrollers, application specific integrated circuits, digital signal processors, programmable logic devices, field programmable gate arrays, and the like, or any combination thereof. In one embodiment, processing unit 920 alone, or possibly in combination with position determination unit 924, may be configured to generate assistance data and to make determinations as to a position of a mobile device, e.g., as described herein.

Memory 922 may be representative of any data storage mechanism. Memory 922 may include, for example, a random access memory, read only memory, etc. While illustrated in this example as being separate from processing unit 920, it should be understood that all or part of memory 922 may be provided within or otherwise co-located/coupled with processing unit 920.

Memory 922 may include in certain instances, one or more data storage devices or systems, such as, for example, a disk drive, an optical disc drive, a tape drive, a solid state memory drive, etc. In certain implementations, memory 922 may be operatively receptive of, or otherwise configurable to couple to, a non-transitory computer-readable medium 940. The non-transitory computer-readable medium 940 may include, for example, any medium that can carry and/or make accessible data, code, instructions, or some combination thereof for the server 900 or possibly for mobile device 800 (FIG. 8). The non-transitory computer-readable medium 940 may also be referred to as a storage medium.

By way of example but not limitation, communications interface 930 may include a network interface device or card, a modem, a router, a switch, a transceiver, and the like. Server 900 may further include, for example, an input/output 932. The input/output 932 may be representative of one or more devices or features that may be configurable to accept or otherwise introduce human and/or machine inputs, and/or one or more devices or features that may be configurable to deliver or otherwise provide for human and/or machine outputs. By way of example but not limitation, the input/output 932 may include an operatively configured display, speaker, keyboard, mouse, trackball, touch screen, data port, etc.

In various embodiments, server 900 may include means for assisting in the determination of a position of a mobile device. For example, server 900 may include means for obtaining a first measurement of a time difference of arrival between a first positioning signal and a second positioning signal as determined by a mobile device (e.g., communications interface 930, processing unit 920, position determination unit 924, and/or memory 922). Server 900 may further include means for receiving a measurement description (e.g., communications interface 930, processing unit 920, position determination unit 924, and/or memory 922). Server 900 may also include means for determining an inter-frequency bias compensation (e.g., position determination unit 924); means for applying the inter-frequency bias compensation to the first measurement (e.g., position determination unit 924); and means for use in determining a position of the mobile device (e.g., position determination unit 924).

Figure 10:
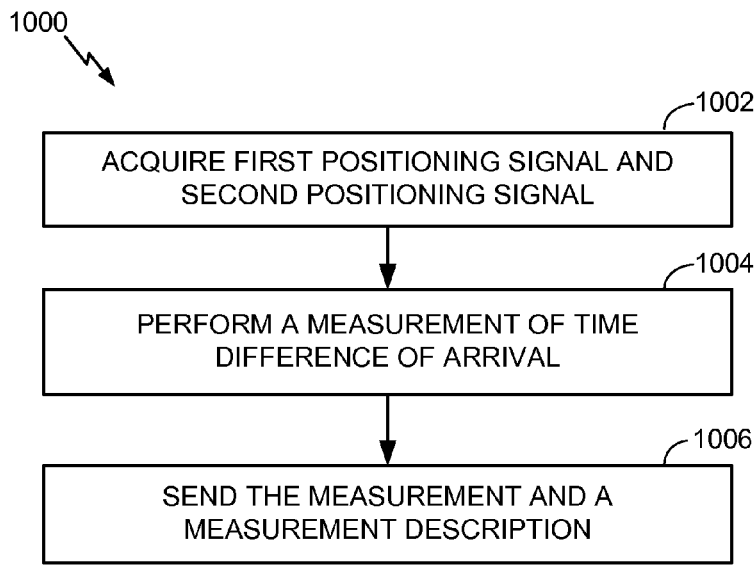
FIG. 10 is a flowchart illustrating an example process for use in a mobile device of determining a position of the mobile device, in accordance with an example implementation.

As described above with reference to process 400 of FIG. 4, in certain implementations, the mobile device may be configured to receive a message (e.g., LPP PROVIDE CAPABILITIES message 706) that indicates whether or not the server (e.g., server 146) has the capability to compensate measurements for the aforementioned inter-frequency related delays. However, in some other implementations the server may not need to indicate such capabilities to the mobile device. That is, in such other implementations, the mobile device may perform uncompensated RSTD measurements, for example, based on already known capabilities of the server. For example, mobile device 136, when operating in wireless communication network 130, may be configured to assume that location server 146 includes the capability to compensate for inter-frequency related delays without the need for additional signaling (e.g., LPP PROVIDE CAPABILITIES message 706) between the mobile device 136 and location server 146. By way of example, FIG. 10 is a flowchart illustrating an example process 1000 for use in a mobile device of determining a position of the mobile device, in accordance with an example implementation.

At process block 1002, a mobile device may acquire a first positioning signal (e.g., positioning signal 202) and a second positioning signal (e.g., positioning signal 204). In one aspect, the mobile device acquires the first and second positioning signals in response to assistance data 102 provided by server 146. As described above, the first positioning signal is transmitted on a first frequency (e.g., F1) and the second positioning signal is transmitted on a second frequency (e.g., F2) that is separate and distinct from the first frequency (e.g., F1≠F2).

At process block 1004, the mobile device may perform a measurement of a time difference of arrival of the pair of first and second positioning signals. In one example, performing the measurement includes performing an Observed Time Difference of Arrival (OTDOA) measurement of the first and second positioning signals. At process block 1004, the measurement is uncompensated for any inter-frequency related delays (e.g., group delay) corresponding to the first frequency (e.g., F1), the second frequency (e.g., F2), or both the first and second frequencies (e.g., F1 and F2). Thus, any initial RSTD determinations made by the mobile device at process block 1004 do not include inter-frequency bias compensation for a difference between the first frequency of the first positioning signal and the second frequency of the second positioning signal, and thus are not compensated for different group delays that may be encountered by the first and/or second positioning signals.

In process block 1006, the mobile device sends the measurement (i.e., uncompensated) to the server. In one aspect, as shown in process block 1006, the mobile device may send, in addition to the measurement, a measurement description to the server. The measurement description may indicate, among other things, that the measurement has not been compensated at the mobile device for the inter-frequency related delays (e.g., mobile device has not applied an inter-frequency bias compensation to the measurement). In one embodiment, sending the measurement description to the server includes sending an LTE Positioning Protocol (LPP) message. The LPP message may include a flag, where the logic state of the flag indicates that the corresponding measurement has not been compensated for the inter-frequency related delays. As described above, the server (e.g., server 146) may then determine the inter-frequency bias compensation of the measurement at the server and determine, at least, the position of the mobile device.

Figure 11:
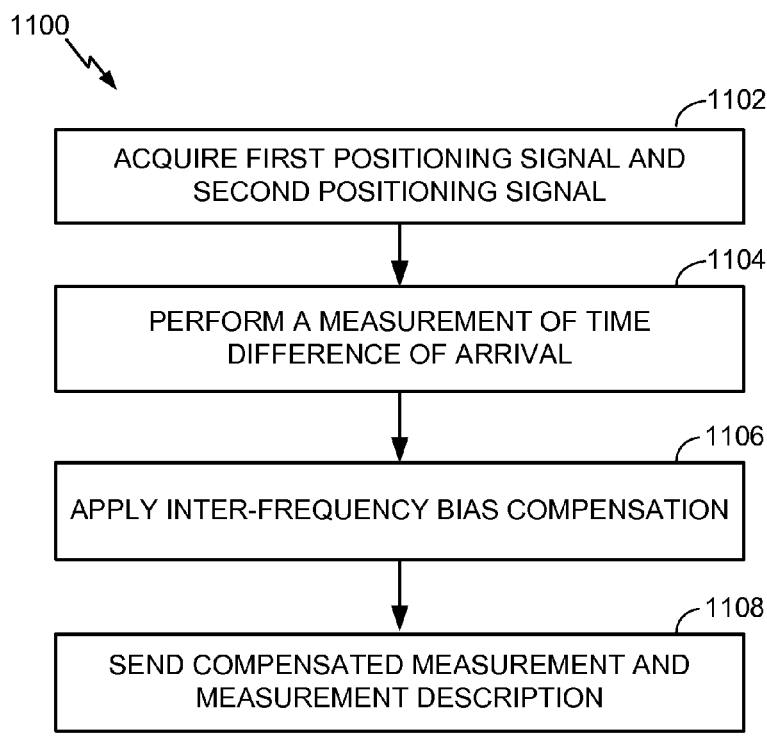
FIG. 11 is a flowchart illustrating another example process for use in a mobile device of determining a position of the mobile device, in accordance with an example implementation.

In other example implementations a mobile device such as mobile device 136, when operating in wireless communication network 130, may be configured to assume that location server 146 does not include the capability to compensate for inter-frequency related delays and thus mobile device 136 may be configured to perform compensated RSTD measurements without the need for additional signaling (e.g., LPP PROVIDE CAPABILITIES message 706) between the mobile device 136 and location server 146. FIG. 11 is a flowchart illustrating such an example process 1100 for use in a mobile device of determining a position of the mobile device, in accordance with an example implementation.

At process block 1102, a mobile device may acquire a first positioning signal (e.g., positioning signal 202) and a second positioning signal (e.g., positioning signal 204). In one aspect, the mobile device acquires the first and second positioning signals in response to assistance data 102 provided by server 146, where the first positioning signal is transmitted on a first frequency (e.g., F1) and the second positioning signal is transmitted on a second frequency (e.g., F2) that is separate and distinct from the first frequency (e.g., F1≠F2).

At process block 1104, the mobile device may perform a measurement of a time difference of arrival of the pair of first and second positioning signals. In one example, performing the measurement includes performing an Observed Time Difference of Arrival (OTDOA) measurement of the first and second positioning signals. At process block 1104, the first measurement is uncompensated for any inter-frequency related delays (e.g., group delay) corresponding to the first frequency (e.g., F1), the second frequency (e.g., F2), or both the first and second frequencies (e.g., F1 and F2). Thus, any initial RSTD determinations made by the mobile device at process block 1104 do not include inter-frequency bias compensation for a difference between the first frequency of the first positioning signal and the second frequency of the second positioning signal, and thus are not compensated for different group delays that may be encountered by the first and/or second positioning signals.

In process block 1106, the mobile device applies an inter-frequency bias compensation to the measurement to generate a compensated measurement. In one example, applying the inter-frequency bias compensation to the measurement at the mobile device includes determining a value of the inter-frequency bias compensation. In certain implementations a mobile device may include a calibration table or other mechanism corresponding to inter-frequency bias compensations for the first and second frequencies that may be applied on an RSTD determination made by the mobile device at process block 1106. In another implementation, the mobile device may (dynamically) calculate an inter-frequency bias compensation at process block 1106. That is, the mobile device may correct or otherwise adjust the measurement for inter-frequency related delays based on a calculated inter-frequency bias compensation, by performing an iterative procedure, such as equation 21, described above to provide an estimated position of the mobile device and the inter-frequency bias compensation. In certain example implementations, the mobile device may be optionally configured to store locally (i.e., at the mobile device) one or more determined inter-frequency bias compensations for use in future RSTD measurements, e.g., to potentially enable the mobile device to update and maintain a more accurate calibration table or other like capability over time.

In process block 1108, the mobile device then sends the compensated measurement to the server, where the server may determine a position of the mobile device based on the compensated measurement. The mobile device may also send, in addition to the compensated measurement, a measurement description to the server. The measurement description of process block 1108 may indicate, among other things, that the compensated measurement has been compensated at the mobile device for the inter-frequency related delays (e.g., mobile device has applied an inter-frequency bias compensation to the first measurement). In one embodiment, sending the measurement description to the server includes sending an LTE Positioning Protocol (LPP) message. The LPP message may include a flag, where the logic state of the flag indicates that the corresponding measurement has been compensated for the inter-frequency related delays. As described above, the server (e.g., server 146) may then determine the position of the mobile device based on the compensated measurement.

Similar to certain aspects described above, the measurement description sent in process block 1108 may include further information to aide or otherwise be utilized by the server in determining the position of the mobile device. For example, the measurement description may further include information indicating a value of the inter-frequency bias compensation that was applied by the mobile device to the measurement in process block 1106. In another implementation, the measurement description may further include a type of the inter-frequency bias compensation that was applied by the mobile device to the measurement in process block 1106. By way of example, the measurement description may indicate that the inter-frequency bias compensation applied by the mobile device was of a type that was retrieved from a calibration table (discussed above), or was of a type that was dynamically calculated (e.g., by way of equation 21). In another implementation, the measurement description may further include a metric, determined by the mobile device, which indicates a reliability or accuracy of the inter-frequency bias compensation applied to the measurement in process block 1106. In yet another implementation, the measurement description indicates an age of the inter-frequency bias compensation that was applied by the mobile device in process block 1106. That is, the age may be indicative of a time that the inter-frequency bias compensation was entered into a calibration table and/or a time that the inter-frequency bias compensation was dynamically calculated by the mobile device. In a further implementation, the measurement description may include at least a portion of data used by the mobile device to perform the measurement of the time difference of arrival. For example, the portion of data used, by the mobile device, to perform the measurement may include a time of arrival (e.g., timestamp) of the first positioning signal, and/or a time of arrival (e.g., timestamp) of the second positioning signal acquired in process block 302.

Those of skill in the art will appreciate that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Further, those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware, firmware, or software in combination with hardware and/or firmware depends upon the particular application and design constraints imposed on the overall system. Skilled artisans may implement the described functionality in varying ways for each particular application, but such implementation decisions should not be interpreted as causing a departure from the scope of the present description.

While the foregoing disclosure shows illustrative embodiments, it should be noted that various changes and modifications could be made herein without departing from the scope of the currently claimed subject matter. The functions, steps and/or actions of the method claims in accordance with the embodiments described herein need not be performed in any particular order. Furthermore, although elements may be described or claimed in the singular, the plural is contemplated unless limitation to the singular is explicitly stated.

What is claimed is:

1. A method for use in a mobile device, the method comprising, at the mobile device:
  acquiring a first positioning signal transmitted at a first frequency and a second positioning signal transmitted at a second frequency that is different than the first frequency;
  performing a first measurement of a time difference of arrival between the first positioning signal and the second positioning signal;
  receiving a message from a server indicating whether the server includes a capability to compensate, at the server, measurements for inter-frequency related delays;
  determining, at the mobile device and based on the received message, whether to apply or not apply an inter-frequency bias compensation to the first measurement for inter-frequency related delays corresponding to the first frequency, the second frequency, or both the first frequency and the second frequency wherein the determining comprises:
    determining to apply the inter-frequency bias compensation to the first measurement, at the mobile device, in response to the message indicating that the server does not include the capability to compensate measurements at the server for the inter-frequency related delays; and
    determining to not apply the inter-frequency bias compensation to the first measurement, at the mobile device, in response to the message indicating the server does include the capability to compensate measurements at the server for the inter-frequency related delays; and
  in response to a determination to not apply the inter-frequency bias compensation, sending the first measurement and a first measurement description to the server to determine a position of the mobile device, wherein the first measurement description indicates that the first measurement has not been compensated, at the mobile device, for the inter-frequency related delays.

2. The method of claim 1, further comprising:
  in response to a determination to apply the inter-frequency bias compensation:
    applying the inter-frequency bias compensation to the first measurement to generate a compensated measurement; and
    sending the compensated measurement and a second measurement description to the server to determine the position of the mobile device, wherein the second measurement description indicates that the compensated measurement has been compensated, at the mobile device, for the inter-frequency related delays.

3. The method of claim 1, wherein receiving the message from the server comprises receiving an LTE Positioning Protocol (LPP) message from the server.

4. The method of claim 1, wherein performing the first measurement comprises performing an Observed Time Difference of Arrival (OTDOA) measurement of the first and second positioning signals.

5. The method of claim 1, wherein the server comprises a location server within a wireless communication network.

6. The method of claim 1, wherein sending the first measurement description to the server further comprises:
  sending an LTE Positioning Protocol (LPP) message to the server.

7. The method of claim 6, wherein sending the LPP message to the server includes controlling a logic state of a flag in the LPP message to indicate that the first measurement has not been compensated for the inter-frequency related delays.

8. A method for use in a mobile device, the method comprising, at the mobile device:
  acquiring a first positioning signal transmitted at a first frequency and a second positioning signal transmitted at a second frequency that is different than the first frequency;
  performing a first measurement of a time difference of arrival between the first positioning signal and the second positioning signal;
  determining, at the mobile device, whether to apply or not apply an inter-frequency bias compensation to the first measurement for inter-frequency related delays corresponding to the first frequency, the second frequency, or both the first frequency and the second frequency; and
  in response to a determination to apply the inter-frequency bias compensation:
    applying the inter-frequency bias compensation to the first measurement to generate a compensated measurement, wherein the applying comprises dynamically calculating, at the mobile device, the inter-frequency bias compensation, wherein dynamically calculating, at the mobile device, comprises performing an iterative procedure that provides a position of the mobile device and the inter-frequency bias compensation, wherein the iterative procedure is performed by estimating an initial estimate and then estimating at least one new estimate based on at least the initial estimate, wherein the at least one new estimate includes the dynamically-calculated inter-frequency bias compensation; and sending the compensated measurement and a second measurement description to the server to determine the position of the mobile device, wherein the second measurement description indicates that the compensated measurement has been compensated, at the mobile device, for the inter-frequency related delays.

9. The method of claim 8, wherein the second measurement description further includes information indicating at least one of:

a value of the inter-frequency bias compensation that is applied, by the mobile device, to the first measurement, a type of the inter-frequency bias compensation that was applied by the mobile device, a metric, determined by the mobile device, indicating a reliability or accuracy of the inter-frequency bias compensation applied by the mobile device, an age of the inter-frequency bias compensation applied by the mobile device, or at least a portion of data used, by the mobile device, to perform the first measurement of the time difference of arrival.

10. The method of claim 9, where the portion of data used, by the mobile device, to perform the first measurement of the time difference of arrival includes at least one of a time of arrival of the first positioning signal, and a time of arrival of the second positioning signal.

11. A mobile device for assisting in the determination of a position of the mobile device in a wireless communication network, the mobile device comprising memory adapted to store program code and a processing unit, coupled to the memory to access and execute instructions included in the program code, and configured to direct the mobile device to:

acquire a first positioning signal transmitted at a first frequency and a second positioning signal transmitted at a second frequency that is different than the first frequency;

perform a first measurement of a time difference of arrival between the first positioning signal and the second positioning signal;

receive a message from a server indicating whether the server includes a capability to compensate, at the server, measurements for inter-frequency related delays;

determine, at the mobile device and based on the received message, whether to apply or not apply an inter-frequency bias compensation to the first measurement for inter-frequency related delays corresponding to the first frequency, the second frequency, or both the first frequency and the second frequency wherein the determining comprises:

determining to apply the inter-frequency bias compensation to the first measurement, at the mobile device, in response to the message indicating that the server does not include the capability to compensate measurements at the server for the inter-frequency related delays; and determining to not apply the inter-frequency bias compensation to the first measurement, at the mobile device, in response to the message indicating the server does include the capability to compensate measurements at the server for the inter-frequency related delays; and in response to a determination to not apply the inter-frequency bias compensation, sending the first measurement and a first measurement description to the server to determine a position of the mobile device, wherein the first measurement description indicates that the first measurement has not been compensated, at the mobile device, for the inter-frequency related delays.

12. The mobile device of claim 11, wherein the program code further comprises instructions to direct the mobile device to:

in response to a determination to apply the inter-frequency bias compensation:

apply the inter-frequency bias compensation to the first measurement to generate a compensated measurement; and send the compensated measurement and a second measurement description to the server to determine the position of the mobile device, wherein the second measurement description indicates that the compensated measurement has been compensated, at the mobile device, for the inter-frequency related delays.

13. The mobile device of claim 11, wherein the instructions to receive the message from the server comprises instructions to receive an LTE Positioning Protocol (LPP) message from the server.

14. The mobile device of claim 11, wherein the instructions to send the first measurement description to the server further comprises instructions to send an LTE Positioning Protocol (LPP) message to the server.

15. The mobile device of claim 14, wherein the instructions to send the LPP message to the server includes instructions to control a logic state of a flag in the LPP message to indicate that the first measurement has not been compensated for the inter-frequency related delays.

16. A mobile device for assisting in the determination of a position of the mobile device in a wireless communication network, the mobile device comprising memory adapted to store program code and a processing unit, coupled to the memory to access and execute instructions included in the program code, and configured to direct the mobile device to:

acquire a first positioning signal transmitted at a first frequency and a second positioning signal transmitted at a second frequency that is different than the first frequency;

perform a first measurement of a time difference of arrival between the first positioning signal and the second positioning signal;

determine, at the mobile device, whether to apply or not apply an inter-frequency bias compensation to the first measurement for inter-frequency related delays corresponding to the first frequency, the second frequency, or both the first frequency and the second frequency; and in response to a determination to apply the inter-frequency bias compensation:

apply the inter-frequency bias compensation to the first measurement to generate a compensated measurement, wherein the applying comprises dynamically calculating, at the mobile device, the inter-frequency bias compensation, wherein the instructions to dynamically calculate, at the mobile device, comprises instructions to perform an iterative procedure that provides the position of the mobile device and the inter-frequency bias compensation, wherein the iterative procedure is performed by estimating an initial estimate and then estimating at least one new estimate based on at least the initial estimate, wherein the at least one new estimate includes the dynamically-calculated inter-frequency bias compensation; and send the compensated measurement and a second measurement description to a server to determine the position of the mobile device, wherein the second measurement description indicates that the compensated measurement has been compensated, at the mobile device, for the inter-frequency related delays.

17. A mobile device for assisting in the determination of a position of the mobile device in a wireless communication network, the mobile device comprising:

means for acquiring a first positioning signal transmitted at a first frequency and a second positioning signal transmitted at a second frequency that is different than the first frequency;

means for performing a first measurement of a time difference of arrival between the first positioning signal and the second positioning signal;

means for receiving a message from a server indicating whether the server includes a capability to compensate, at the server, measurements for inter-frequency related delays;

means for determining, at the mobile device and based on the received message, whether to apply or not apply an inter-frequency bias compensation to the first measurement for inter-frequency related delays corresponding to the first frequency, the second frequency, or both the first frequency and the second frequency wherein the determining comprises:

determining to apply the inter-frequency bias compensation to the first measurement, at the mobile device, in response to the message indicating that the server does not include the capability to compensate measurements at the server for the inter-frequency related delays; and determining to not apply the inter-frequency bias compensation to the first measurement, at the mobile device, in response to the message indicating the server does include the capability to compensate measurements at the server for the inter-frequency related delays; and means for sending, in response to a determination to not apply the inter-frequency bias compensation, the first measurement and a first measurement description to the server to determine the position of the mobile device, wherein the first measurement description indicates that the first measurement has not been compensated, at the mobile device, for the inter-frequency related delays.

18. The mobile device of claim 17, further comprising:
means for applying, in response to a determination to apply the inter-frequency bias compensation, the inter-frequency bias compensation to the first measurement to generate a compensated measurement; and means for sending the compensated measurement and a second measurement description to the server to determine the position of the mobile device, wherein the second measurement description indicates that the compensated measurement has been compensated, at the mobile device, for the inter-frequency related delays.

19. A non-transitory computer-readable medium including program code stored thereon for use in determining a position of a mobile device in a wireless communication network, the program code comprising instructions to:

acquire a first positioning signal transmitted at a first frequency and a second positioning signal transmitted at a second frequency that is different than the first frequency;

perform a first measurement of a time difference of arrival between the first positioning signal and the second positioning signal;

receive a message from a server indicating whether the server includes a capability to compensate, at the server, measurements for inter-frequency related delays;

determine, at the mobile device and based on the received message, whether to apply or not apply an inter-frequency bias compensation to the first measurement for inter-frequency related delays corresponding to the first frequency, the second frequency, or both the first frequency and the second frequency wherein the determining comprises:

determining to apply the inter-frequency bias compensation to the first measurement, at the mobile device, in response to the message indicating that the server does not include the capability to compensate measurements at the server for the inter-frequency related delays; and determining to not apply the inter-frequency bias compensation to the first measurement, at the mobile device, in response to the message indicating the server does include the capability to compensate measurements at the server for the inter-frequency related delays; and in response to a determination to not apply the inter-frequency bias compensation, sending the first measurement and a first measurement description to the server to determine the position of the mobile device, wherein the first measurement description indicates that the first measurement has not been compensated, at the mobile device, for the inter-frequency related delays.

20. The non-transitory computer-readable medium of claim 19, wherein the program code further comprises instructions to:

in response to a determination to apply the inter-frequency bias compensation:

apply the inter-frequency bias compensation to the first measurement to generate a compensated measurement; and send the compensated measurement and a second measurement description to the server to determine the position of the mobile device, wherein the second measurement description indicates that the compensated measurement has been compensated, at the mobile device, for the inter-frequency related delays.

21. A method for use in a mobile device, the method comprising, at the mobile device:

acquiring a first positioning signal transmitted at a first frequency and a second positioning signal transmitted at a second frequency that is different than the first frequency;

performing a measurement of a time difference of arrival between the first positioning signal and the second positioning signal; and applying an inter-frequency bias compensation to the measurement to generate a compensated measurement, wherein the applying comprises dynamically calculating, at the mobile device, the inter-frequency bias compensation, wherein dynamically calculating, at the mobile device, comprises performing an iterative procedure that provides a position of the mobile device and the inter-frequency bias compensation, wherein the iterative procedure is performed by estimating an initial estimate and then estimating at least one new estimate based on at least the initial estimate, wherein the at least one new estimate includes the dynamically-calculated inter-frequency bias compensation; and sending the compensated measurement and a measurement description to a location server, wherein the measurement description indicates that the compensated measurement has been compensated, at the mobile device, for inter-frequency related delays.

22. An apparatus for use in a mobile device, the apparatus comprising:

means for acquiring a first positioning signal transmitted at a first frequency and a second positioning signal transmitted at a second frequency that is different than the first frequency;

means for performing a measurement of a time difference of arrival between the first positioning signal and the second positioning signal; and means for applying an inter-frequency bias compensation to the measurement to generate a compensated measurement, wherein the applying comprises dynamically calculating, at the mobile device, the inter-frequency bias compensation, wherein dynamically calculating, at the mobile device, comprises performing an iterative procedure that provides a position of the mobile device and the inter-frequency bias compensation, wherein the iterative procedure is performed by estimating an initial estimate and then estimating at least one new estimate based on at least the initial estimate, wherein the at least one new estimate includes the dynamically-calculated inter-frequency bias compensation; and means for sending the compensated measurement and a measurement description to a location server, wherein the measurement description indicates that the compensated measurement has been compensated, at the mobile device, for inter-frequency related delays.

23. An apparatus for use in a mobile device, the apparatus comprising memory adapted to store program code and a processing unit, coupled to the memory to access and execute instructions included in the program code, and configured to direct the mobile device to:

acquire a first positioning signal transmitted at a first frequency and a second positioning signal transmitted at a second frequency that is different than the first frequency;

perform a measurement of a time difference of arrival between the first positioning signal and the second positioning signal; and apply an inter-frequency bias compensation to the measurement to generate a compensated measurement, wherein the applying comprises dynamically calculating, at the mobile device, the inter-frequency bias compensation, wherein dynamically calculating, at the mobile device, comprises performing an iterative procedure that provides a position of the mobile device and the inter-frequency bias compensation, wherein the iterative procedure is performed by estimating an initial estimate and then estimating at least one new estimate based on at least the initial estimate, wherein the at least one new estimate includes the dynamically-calculated inter-frequency bias compensation; and send the compensated measurement and a measurement description to a location server, wherein the measurement description indicates that the compensated measurement has been compensated, at the mobile device, for inter-frequency related delays.

24. A non-transitory computer-readable medium including program code stored thereon for use in determining a position of a mobile device in a wireless communication network, the program code comprising instructions to:

acquire a first positioning signal transmitted at a first frequency and a second positioning signal transmitted at a second frequency that is different than the first frequency;

perform a measurement of a time difference of arrival between the first positioning signal and the second positioning signal;

apply an inter-frequency bias compensation to the measurement to generate a compensated measurement, wherein the applying comprises dynamically calculating, at the mobile device, the inter-frequency bias compensation, wherein dynamically calculating, at the mobile device, comprises performing an iterative procedure that provides the position of the mobile device and the inter-frequency bias compensation, wherein the iterative procedure is performed by estimating an initial estimate and then estimating at least one new estimate based on at least the initial estimate, wherein the at least one new estimate includes the dynamically-calculated inter-frequency bias compensation; and send the compensated measurement and a measurement description to a location server, wherein the measurement description indicates that the compensated measurement has been compensated, at the mobile device, for inter-frequency related delays.

25. A mobile device for assisting in the determination of a position of the mobile device in a wireless communication network, the mobile device comprising:

means for acquiring a first positioning signal transmitted at a first frequency and a second positioning signal transmitted at a second frequency that is different than the first frequency;

means for performing a first measurement of a time difference of arrival between the first positioning signal and the second positioning signal;

means for determining, at the mobile device, whether to apply or not apply an inter-frequency bias compensation to the first measurement for inter-frequency related delays corresponding to the first frequency, the second frequency, or both the first frequency and the second frequency; and means for applying, in response to a determination to apply the inter-frequency bias compensation, the inter-frequency bias compensation to the first measurement to generate a compensated measurement, wherein the applying comprises dynamically calculating, at the mobile device, the inter-frequency bias compensation, wherein dynamically calculating, at the mobile device, comprises performing an iterative procedure that provides the position of the mobile device and the inter-frequency bias compensation, wherein the iterative procedure is performed by estimating an initial estimate and then estimating at least one new estimate based on at least the initial estimate, wherein the at least one new estimate includes the dynamically-calculated inter-frequency bias compensation; and sending the compensated measurement and a second measurement description to a server to determine the position of the mobile device, wherein the second measurement description indicates that the compensated measurement has been compensated, at the mobile device, for the inter-frequency related delays.

26. A non-transitory computer-readable medium including program code stored thereon for use in determining a position of a mobile device in a wireless communication network, the program code comprising instructions to:
  acquire a first positioning signal transmitted at a first frequency and a second positioning signal transmitted at a second frequency that is different than the first frequency;
  perform a first measurement of a time difference of arrival between the first positioning signal and the second positioning signal;
  determine, at the mobile device, whether to apply or not apply an inter-frequency bias compensation to the first measurement for inter-frequency related delays corresponding to the first frequency, the second frequency, or both the first frequency and the second frequency; and
  in response to a determination to apply the inter-frequency bias compensation:
    apply the inter-frequency bias compensation to the first measurement to generate a compensated measurement, wherein the applying comprises dynamically calculating, at the mobile device, the inter-frequency bias compensation, wherein dynamically calculating, at the mobile device, comprises performing an iterative procedure that provides the position of the mobile device and the inter-frequency bias compensation, wherein the iterative procedure is performed by estimating an initial estimate and then estimating at least one new estimate based on at least the initial estimate, wherein the at least one new estimate includes the dynamically-calculated inter-frequency bias compensation; and
  send the compensated measurement and a second measurement description to a server to determine the position of the mobile device, wherein the second measurement description indicates that the compensated measurement has been compensated, at the mobile device, for the inter-frequency related delays.

* * * * *